United States Patent
Gordon

(10) Patent No.: US 11,889,817 B2
(45) Date of Patent: Feb. 6, 2024

(54) SUBSTANCE DELIVERY DEVICE

(71) Applicant: TG Medwise Ltd., Hod HaSharon (IL)

(72) Inventor: Tal Gordon, Hod Hasharon (IL)

(73) Assignee: TG Medwise Ltd., Kefar Malal (IL)

( * ) Notice: Subject to any disclaimer, the term of this patent is extended or adjusted under 35 U.S.C. 154(b) by 28 days.

(21) Appl. No.: 16/404,895

(22) Filed: May 7, 2019

(65) Prior Publication Data
US 2019/0254797 A1    Aug. 22, 2019

Related U.S. Application Data

(63) Continuation-in-part of application No. 14/419,245, filed as application No. PCT/US2013/054633 on Aug. 13, 2013, now abandoned.

(51) Int. Cl.
| | | |
|---|---|---|
| A01K 27/00 | (2006.01) | |
| A61D 7/00 | (2006.01) | |
| A61M 35/00 | (2006.01) | |
| A01K 13/00 | (2006.01) | |

(52) U.S. Cl.
CPC .......... *A01K 27/007* (2013.01); *A01K 27/009* (2013.01); *A01K 13/003* (2013.01); *A61D 7/00* (2013.01); *A61M 35/10* (2019.05); *A61M 2205/13* (2013.01); *A61M 2205/3317* (2013.01); *A61M 2230/50* (2013.01); *A61M 2250/00* (2013.01)

(58) Field of Classification Search
CPC ........................... A01K 27/007; A01K 27/009
See application file for complete search history.

(56) References Cited

U.S. PATENT DOCUMENTS

| | | | | | |
|---|---|---|---|---|---|
| 4,068,624 | A | * | 1/1978 | Ramney | A01K 27/007 119/654 |
| 4,513,891 | A | * | 4/1985 | Hain | A61M 15/08 222/213 |
| 4,902,154 | A | * | 2/1990 | Valenza | A01K 13/002 119/664 |
| 5,980,496 | A | * | 11/1999 | Jacobsen | A01K 27/007 604/289 |
| 6,349,232 | B1 | * | 2/2002 | Gordon | A01K 27/009 604/20 |
| 6,588,376 | B1 | * | 7/2003 | Groh | A01K 15/022 119/718 |

(Continued)

FOREIGN PATENT DOCUMENTS

| | | |
|---|---|---|
| JP | 2006-500508 | 1/2006 |
| JP | 2007-530860 | 11/2007 |

(Continued)

*Primary Examiner* — Jessica B Wong
(74) *Attorney, Agent, or Firm* — Dekel Patent Ltd.; David Klein

(57) ABSTRACT

A delivery device includes a collar device for wearing on an animal, a dosing probe disposed on the collar device for delivering a substance therefrom, an actuator configured to deliver the substance from the dosing probe through an opening formed in the dosing probe, a controller in communication with the actuator and configured to control delivery of the substance from the dosing probe, and a sensor in communication with the controller and configured to sense that the collar device is touching fur or skin of the animal and the dosing probe is directed towards fur or skin of the animal.

7 Claims, 25 Drawing Sheets

(56) References Cited

U.S. PATENT DOCUMENTS

| | | | | |
|---|---|---|---|---|
| 7,992,525 B1* | 8/2011 | Fisher | ............... | A01K 15/02 |
| | | | | 119/860 |
| 2002/0109599 A1* | 8/2002 | Aull | ............... | A01K 15/02 |
| | | | | 340/573.1 |
| 2006/0271020 A1 | 11/2006 | Huang | | |
| 2007/0095304 A1* | 5/2007 | Rosenberg | ............. | A01K 29/00 |
| | | | | 119/720 |
| 2010/0152812 A1* | 6/2010 | Flaherty | ............. | A61N 1/36103 |
| | | | | 607/50 |
| 2011/0132275 A1* | 6/2011 | Huo | ............... | A01K 27/009 |
| | | | | 119/720 |
| 2014/0123912 A1* | 5/2014 | Menkes | ............. | A61B 5/02055 |
| | | | | 119/859 |

FOREIGN PATENT DOCUMENTS

| | | |
|---|---|---|
| WO | 00/26537 | 5/2000 |
| WO | 2002/083204 | 10/2002 |
| WO | 2004/029457 | 4/2004 |
| WO | 2005/094919 | 10/2005 |

* cited by examiner

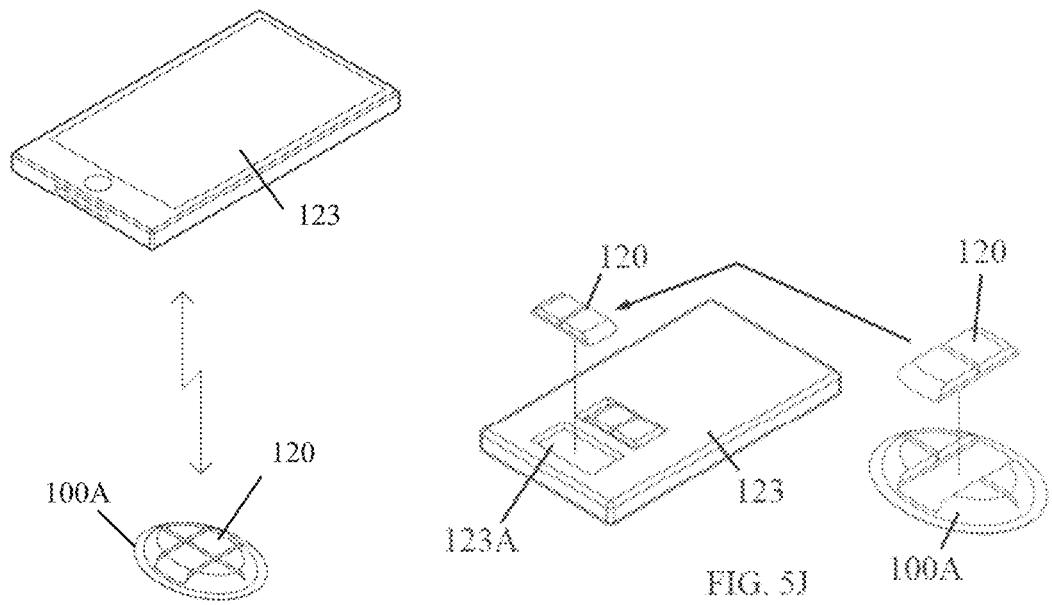
FIG. 5I
FIG. 5J
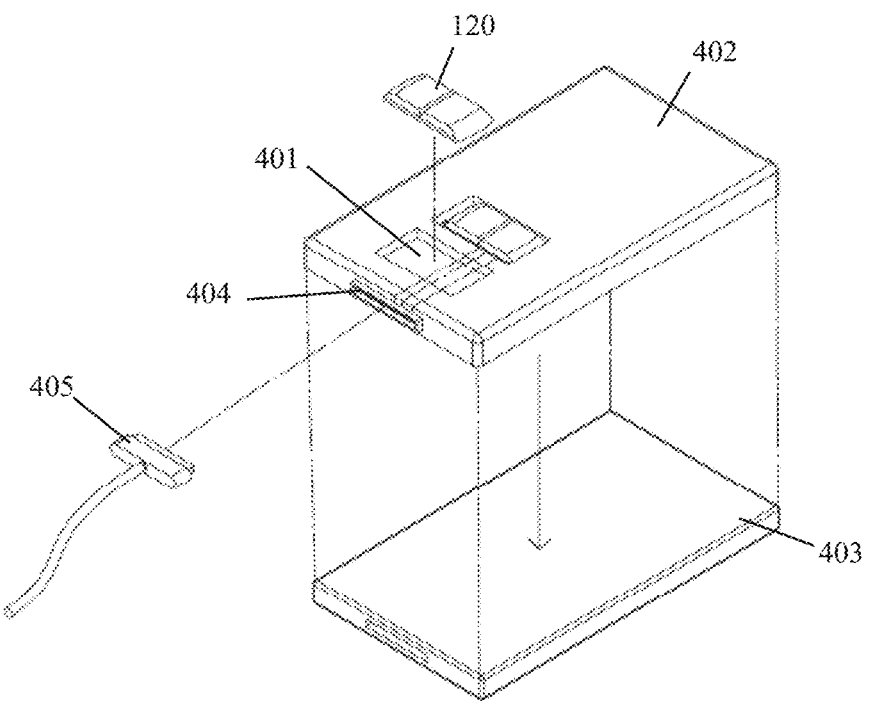
FIG. 5K

SUBSTANCE DELIVERY DEVICE

CROSS-REFERENCE TO OTHER APPLICATIONS

This application claims priority from U.S. Provisional Patent Application 61/682,317, filed Aug. 13, 2012, PCT Patent Application PCT/US2013/054633, filed Aug. 13, 2013, and from U.S. patent application Ser. No. 14/419,245, filed Feb. 3, 2015, which are incorporated herein by reference.

FIELD OF THE INVENTION

The present invention relates generally to delivery devices for substances, such as but not limited to, drugs and pharmaceuticals.

BACKGROUND OF THE INVENTION

There are many kinds of drug delivery devices. Some well-known devices include infusion pumps and transdermal delivery devices. Ultrasound has been used to rupture microcapsules for effecting drug release therefrom. Biodegradable hydrogels and temperature sensitive hydrophilic polymer gels or hydrogels have been used as carriers for biologically active materials such as hormones, enzymes, and antibiotics.

SUMMARY OF THE INVENTION

The present invention seeks to provide improved delivery devices for substances, such as but not limited to, drugs, pharmaceuticals, scents and deodorizers, as described more in detail herein below. The terms "substance" and "drugs" are used interchangeably throughout and it is noted that these terms encompass more than just a drug, pharmaceutical, scent or deodorizer, but also any chemical used to effect a desired result. The delivery devices of the invention may be of any size and shape, such as but not limited to, in the range of millimeters up to centimeters. The delivery devices of the invention may be drug delivery pumps, such as but not limited to, insulin delivery pumps.

In accordance with a non-limiting embodiment of the present invention, the delivery device is flexible, bendable and encapsulated with a conformal coating that protects it from possible environmental or other kinds of damage, and also protects the user from adverse effects from internal components of the device. "Bendable" and "flexible" means capable of being bent or flexed by normal human movement, such as being bent or flexed by fingers or other body parts. The flexible device conforms to the patient's body and is pleasant to the touch. A membrane assembly, described below, is used to dispense the substance. A soft, pliant bag or any other suitable container or reservoir contains the substance to be delivered, such as but not limited to, insulin or flea control substances and many more. In the case of a pliant reservoir (e.g., bag), the reservoir collapses to a flat state upon emptying the substance from it. The device can be used to deliver multiple substances, at the same time or at time intervals, using dependent or independent dosing protocols that control quantities and timing.

It is noted that throughout the specification and claims, the term "membrane" encompasses any suitable partition that responds to a force or pressure applied on one side of the membrane to transfer a force or pressure to the other side of the membrane, such as but not limited to, a membrane, partition, bellows, diaphragm, Belleville washer, tube and the like. The membrane is preferably resilient or flexible, but in certain applications the membrane can be rigid or semi-rigid.

In accordance with a non-limiting embodiment of the present invention, the delivery device has an actuating chamber with an actuating substance, sealed by a chamber membrane. A dosing chamber contains the substance to be delivered, sealed by a substance-delivery membrane. A separation element is located between the chamber membrane and the substance-delivery membrane. Upon expansion of the actuating substance, the chamber membrane pushes the separation element against the substance-delivery membrane to deliver the substance. The separation element is sealed tight against the chamber membrane so as to prevent liquid or vapor from leaking past the chamber membrane to the substance. This prevents any possible leaking due permeability of the membrane material. The separation element thus provides not only physical insulation (separation), but also thermal insulation, so the substance to be delivered is not affected by heating or cooling of the actuating substance, and electrical insulation.

In accordance with a non-limiting embodiment of the present invention, the heating element of the delivery device is mounted directly on a printed circuit board (PCB) or is a portion of one or more layers of the PCB. Alternatively, the heating element of the delivery device may be a resistive element disposed in (and may be electrically insulated from) the actuating substance.

The more actuating substance in the actuating chamber, the more energy is needed to heat the actuating substance to expand it (e.g., to vaporize it). A well designed device will contain a sufficient amount of actuating substance (e.g., heating liquid) in the actuating chamber to allow sufficient pressure and pushing force, yet small enough to minimize the heating energy required. To optimize the energy efficiency of the device, yet another non-limiting embodiment of the present invention is presented.

In accordance with this other non-limiting embodiment of the present invention, the actuating chamber contains a sufficient, yet minimal amount of actuating substance (e.g., heating liquid), so that the required heating energy is minimal. A reservoir containing additional actuating substance (e.g., heating liquid) is next to the heating chamber. Means to replenish "lost" actuating substance in the actuating chamber are provided, thus allowing maintaining a sufficient level/amount of actuating substance within the chamber over long periods of time even if any actuating substance is lost over time.

As described below, one way of accomplishing this is with a reservoir with low positive pressure plus a directional valve allowing entrance of actuating liquid into the chamber. Another way is to use a reservoir with low positive pressure which is sealed by a membrane which is constrained to remain stationary. The membrane has low permeability to allow slow entrance of liquid over time, to replenish the "lost" liquid within the chamber.

There is provided in accordance with an embodiment of the present invention a delivery device including a drug delivery pump including a dosing chamber for delivering a substance therefrom, pushing apparatus, a thermal energy source arranged to cause a sufficient change in temperature in a portion of the pushing apparatus so that the pushing apparatus imparts a pushing force against the substance to cause the substance to be delivered from the dosing chamber, a controller for controlling delivery of the substance from the dosing chamber, and a thermal insulator that thermally insulates the substance in the dosing chamber from the thermal energy source.

There is provided in accordance with an embodiment of the present invention a delivery device including a drug delivery pump including a dosing chamber for delivering a substance therefrom, a reservoir in fluid communication with the dosing chamber, pushing apparatus, an actuator operatively linked to the pushing apparatus to cause the pushing apparatus to impart a pushing force against the substance to cause the substance to be delivered from the dosing chamber, a controller for controlling delivery of the substance from the dosing chamber, and a limiter that limits compression of the substance in the dosing chamber.

There is provided in accordance with an embodiment of the present invention a delivery device including a collar device for wearing on an animal, the collar device including a dosing chamber for delivering a substance therefrom, an actuator for causing the substance to be delivered from the dosing chamber, a controller for controlling delivery of the substance from the dosing chamber, and a probe protruding from the collar towards skin of the animal.

There is provided in accordance with an embodiment of the present invention a delivery device including a collar device for wearing on an animal, the collar device including a dosing chamber for delivering a substance therefrom, pushing apparatus, a controller for controlling delivery of the substance from the dosing chamber, and a thermal energy source arranged to cause a sufficient change in temperature in a portion of the pushing apparatus so that the pushing apparatus imparts a pushing force against the substance to cause the substance to be delivered from the dosing chamber.

There is provided in accordance with an embodiment of the present invention a delivery device including a dosing chamber for delivering a substance therefrom, an actuator for causing the substance to be delivered from the dosing chamber, a flexible and bendable external housing in which the dosing chamber and the actuator are housed, a cannula or needle protrudable from the housing to penetrate into skin, and a fluid conduit in fluid communication between the dosing chamber and the cannula or needle.

In accordance with an embodiment of the present invention a sensor is operative to sense a rate of delivering the substance from the dosing chamber. The sensor communicates with the controller, and the controller is operative to detect clogging or leaking in accordance with information sensed by the sensor.

In accordance with an embodiment of the present invention the dosing chamber includes a substance-delivery membrane, and the pushing apparatus includes a pusher element arranged to push against the substance-delivery membrane to cause the substance to be delivered from the dosing chamber, and the pushing apparatus also includes an actuating chamber containing an actuating substance capable of imparting a force on the pusher element upon a suitable change in temperature and volume of the actuating substance.

In accordance with an embodiment of the present invention the actuating substance includes a fluid and a chamber membrane separates the fluid from the pusher element.

In accordance with an embodiment of the present invention the pusher element thermally insulates the substance in the dosing chamber from the actuating substance.

In accordance with an embodiment of the present invention the actuating chamber is sealed so that the actuating substance is prevented from leaking into the substance in the dosing chamber.

In accordance with an embodiment of the present invention the actuating chamber includes a maintaining element arranged to maintain the actuating substance in conductive thermal contact with the thermal energy source in any gravitational orientation.

In accordance with an embodiment of the present invention a filling device is operatively connected to the actuating chamber for maintaining a necessary amount of the actuating substance in the actuating chamber.

In accordance with an embodiment of the present invention the pushing apparatus includes a piston arranged to push against the substance to be delivered from the dosing chamber, and the pushing apparatus also includes an actuating chamber containing an actuating substance capable of imparting a force on the piston upon a suitable change in temperature of the actuating substance.

In accordance with an embodiment of the present invention the pushing apparatus includes a Belleville washer.

In accordance with an embodiment of the present invention the delivery device further includes a plurality of dosing chambers.

In accordance with an embodiment of the present invention different substances are delivered from the dosing chamber.

In accordance with an embodiment of the present invention a displacement sensor is operative to sense displacement of the pushing apparatus.

In accordance with an embodiment of the present invention the delivery device is encapsulated in a protective coating.

In accordance with an embodiment of the present invention the delivery device is flexible and bendable.

BRIEF DESCRIPTION OF THE DRAWINGS

The present invention will be understood and appreciated more fully from the following detailed description, taken in conjunction with the drawings in which:

FIGS. 4B and 4C are simplified sectional illustrations of a delivery device that includes a plurality of dosing chambers, constructed and operative in accordance with a non-limiting embodiment of the present invention, wherein each individual dosing chamber may be constructed like the dosing chamber of FIG. 4A, and wherein FIGS. 4B and 4C are taken along lines 4B-4B and 4C-4C, respectively, in FIG. 4A;

FIGS. 5I, 5J and 5K are simplified pictorial illustrations of a reusable portion of the delivery device, which may be inserted in a user control unit, in accordance with a non-limiting embodiment of the present invention;

FIGS. 12A-12D are simplified illustrations of an actuating chamber, in accordance with a non-limiting embodiment of the present invention, wherein FIG. 12A shows the chamber is a closed cushion or pliant, resilient closure, FIGS. 12B and 12C illustrate the chamber respectively before and after the actuating substance is heated and expanded, and FIG. 12D shows the actuating chamber used to push a piston or separator;

FIGS. 14A-14F are simplified illustrations of another embodiment of the invention, wherein the delivery device has a cannula mounted on a flexible mounting member, in accordance with a non-limiting embodiment of the present invention, wherein FIGS. 14A and 14B are side views, 14C and 14D are top views, respectively in rest and strained positions, and 14E and 14F are top views, respectively in rest and strained positions.

DESCRIPTION OF EMBODIMENTS OF THE INVENTION

Reference is now made to FIGS. 1A-3A, which illustrate a delivery device 10, constructed and operative in accordance with a non-limiting embodiment of the present invention. In the illustrated embodiment, delivery device 10 is a miniature device constructed of multiple layers, which makes for an easy and inexpensive manufacturing and assembly. However, the device is not limited to such a construction.

Delivery device 10 includes a base 11, at least part of which is occupied by a PCB 12, on which is mounted a thermal energy source 14, such as but not limited to, one or more resistors or any other kind of resistive heating elements, or thermoelectric components. Non-limiting examples include a thermal resistor, or a layer of resistive material such as graphite or thin metal laid on the PCB as part of the PCB manufacturing processes, or a segment of electrical conductors on the PCB. Electrical current running through the thermal resistor/resistance-material heats it up, and heat is transferred to the actuating substance (described next) by thermal conduction, convection or radiation (or combinations thereof, depending on the material) PCB 12 may extend beyond what is shown in FIGS. 1A-3A. PCB 12 may also include a battery, a controller (such as control logic circuitry or microprocessor and the like), sensors, wireless communications and other electronic components (not shown here), for powering and controlling delivery device 10.

Figure 3A:
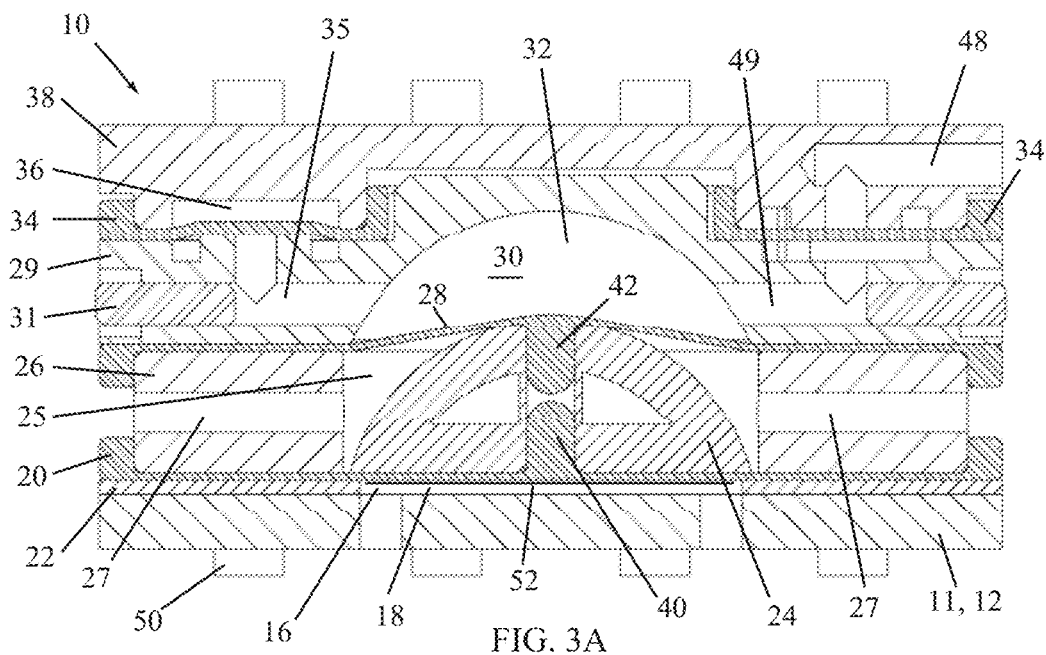
FIGS. 3A, 3B and 3C are simplified sectional illustrations of the delivery device, taken along lines A-A in FIG. 2, respectively, before, during and after moving a separation element against a membrane to dispense a substance from the delivery device in accordance with a non-limiting embodiment of the present invention.

As seen in FIG. 3A, device 10 includes an actuating chamber 16 containing an actuating substance 18, such as but not limited to, a fluid, e.g., water, methanol, hexane or alcohol or others, which may undergo a phase change from liquid to gas or from gas to liquid, or a solid phase-change material with a high change in volume, e.g., inorganic salt hydrates. The actuating chamber 16 may be formed by a chamber membrane 20 which overlies base 11, separated therefrom by a spacer 22. The chamber membrane 20, with or without the addition of the spacer 22, seals the actuating substance 18 in actuating chamber 16.

As seen best in FIG. 3A, a separation element 24 rests against chamber membrane 20. Separation element 24 may be made of any suitably medically safe material, such as plastic or metal (with a poor thermal conductivity); element 24 may be hollow (to increase thermal insulation). In the illustrated embodiment, separation element 24 is a partial sphere, but it can have other shapes as well. Separation element 24 sits in an aperture 25 formed in an intermediate member 26. Separation element 24 is arranged to push against a substance-delivery membrane 28 (also referred to as pushing apparatus), which is sandwiched between intermediate member 26 and a dose base 29, in which is formed a dosing chamber 30. In the illustrated embodiment, separation element 24 is attached to chamber membrane 20 by means of a lug 40 protruding from membrane 20. Likewise, separation element 24 is attached to substance-delivery membrane 28 by means of a lug 42 protruding from membrane 28. The lugs sit snugly in suitable apertures formed in separation element 24.

A substance 32, such as but not limited to, drugs for human or animal use, is contained in dosing chamber 30. The substance-delivery membrane 28 seals substance 32 in dosing chamber 30. Dosing chamber 30 may also be sealed by one or more plugs 31. The substance 32 can exit dosing chamber 30 (in a manner about to be described below, and in further embodiments described with reference to the series of FIGS. 11 and 13) via a conduit 35 (FIGS. 3A, 3B and 3D), which is initially covered by a valve membrane 34. The pressure of the flowing substance 32, induced by the separation element 24, pushes up and opens valve membrane 34, and substance 32 flows out of one or more exit ports 36 formed in a cover 38.

A soft, pliant bag or any other suitable container or reservoir 44 (shown in FIG. 1A) contains the substance 32 to be delivered. Container 44 preferably, but not necessarily, collapses to a flat state after substance 32 is evacuated therefrom. Substance 32 may be introduced from container 44 by negative pressure as follows. When substance-delivery membrane 28 moves downwards in the sense of FIG. 3A (returning from its position in FIG. 3C), it creates a negative pressure in dosing chamber 30. This pressure causes the inlet valve membrane 34 to open and causes the substance 32 to be drawn (sucked) from container 44; the substance 32 flows through one or more inlet ports 48 via passages 49 to dosing chamber 30. Any other suitable means of attaching container 44 to device 10 and drawing the substance 32 from container 44 may be implemented.

The layered assembly of device 10 may be secured by fasteners 50 (FIGS. 1A-1B), such as posts or other mechanical elements, or by bonding or other means of joining.

Chamber membrane 20 and/or substance-delivery membrane 28 may be a "bellows" type of membrane (like in FIG. 11E), i.e., including folds that stretch out and fold back upon expansion and contraction, respectively. Alternatively, the membranes (20 and/or 28) may be Belleville washers (like in FIG. 11F), which "snap" from one position to another.

Figure 3B:
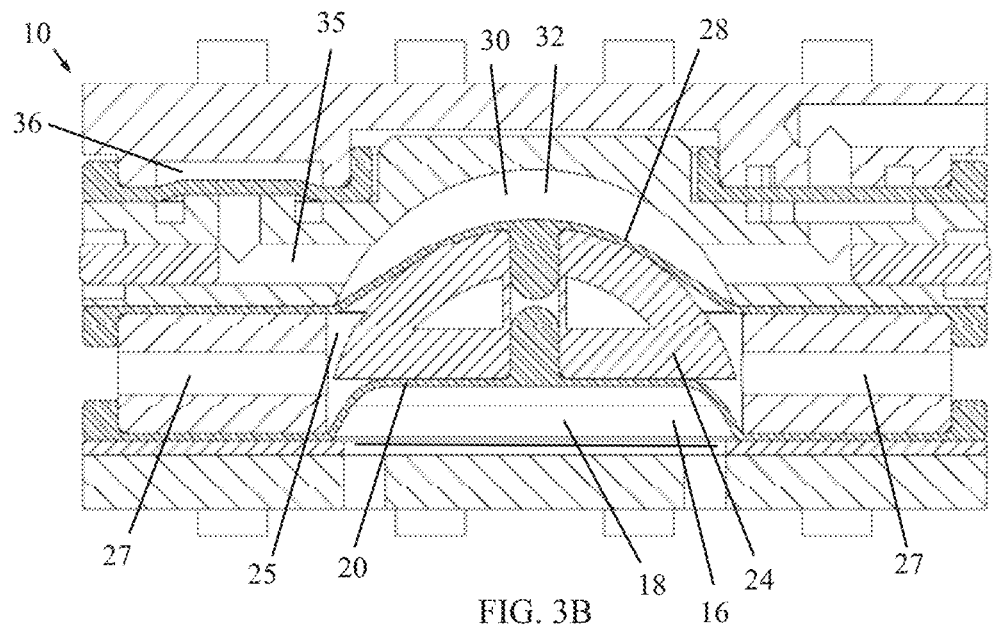
Figure 3C:
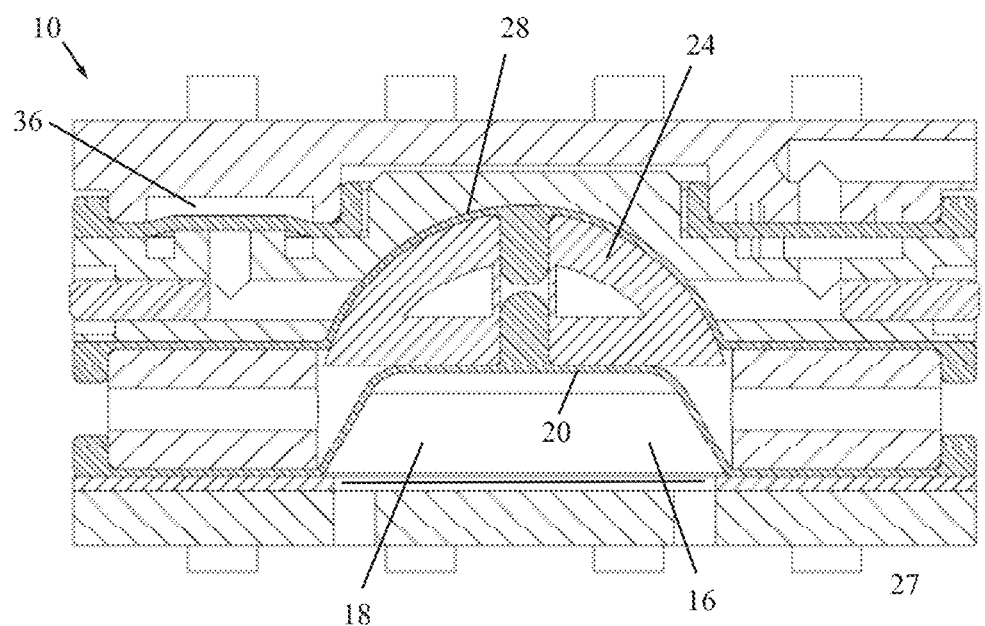
Figures 3D, 3E:
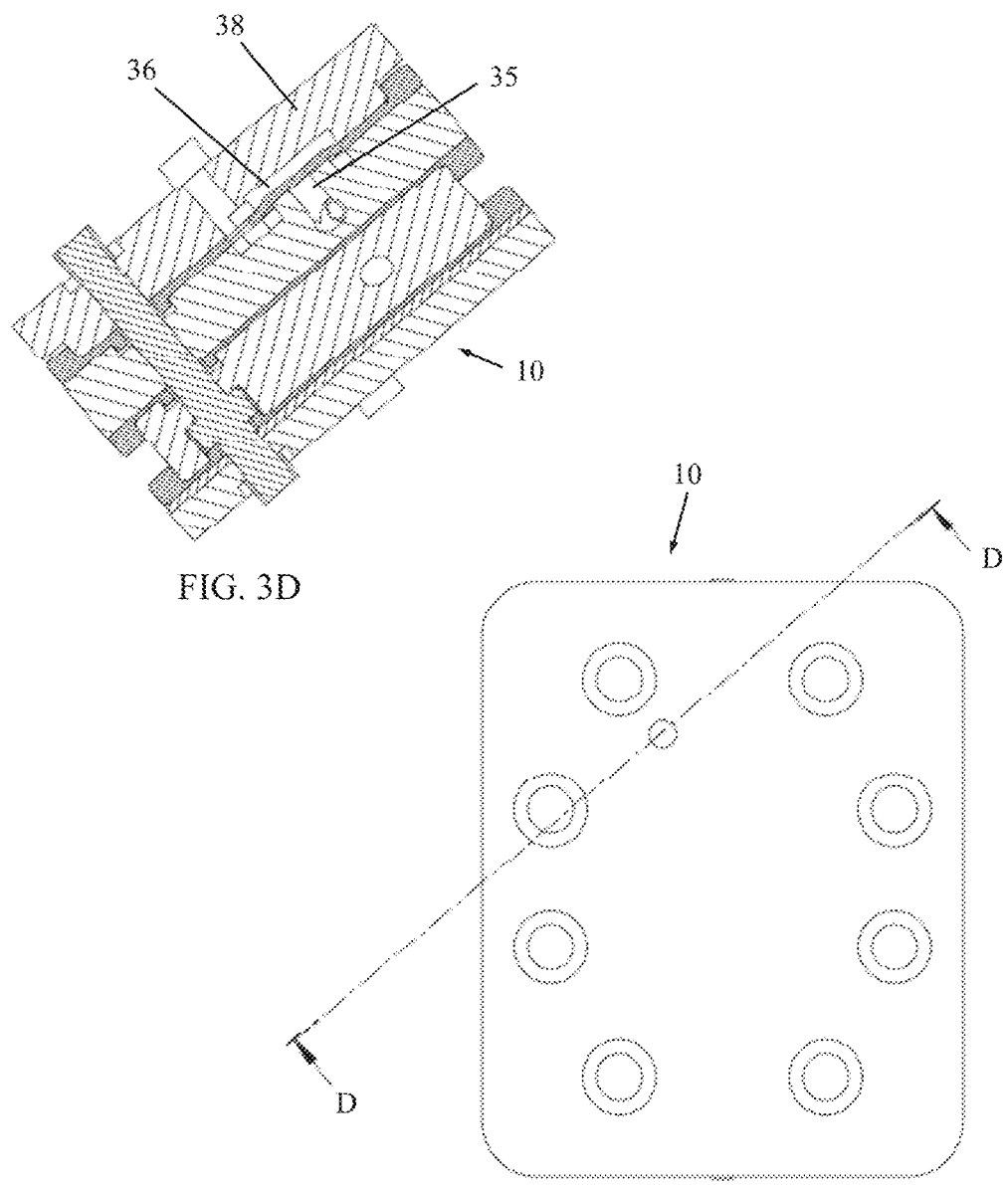
FIG. 3D is a simplified top-view illustration of the delivery device.
FIG. 3E is a simplified sectional illustration of the delivery device, taken along lines D-D in FIG. 3D.

In operation, thermal energy source 14 is energized (by a battery, not shown) and controlled (by a controller, not shown) to heat actuating substance 18 so that the temperature change is sufficient to cause a volumetric change (e.g., expansion) in actuating substance 18. In one embodiment, the sufficient temperature change causes a phase change in actuating substance 18 (e.g., solid-liquid or liquid-gas); alternatively, no phase change occurs (e.g., heating a gas, such as air). As seen in FIG. 3B, the expanding actuating substance 18 pushes against chamber membrane 20, which in turn pushes against separation element 24. Separation element 24 pushes against substance-delivery membrane 28, which in turn pushes against substance 32, thereby causing substance 32 to be delivered out of dosing chamber 30. In FIG. 3C, substance 32 has been completely delivered out of dosing chamber 30. After the dosage, the actuating substance 18 cools and separation element 24 returns to the position of FIG. 3A, thereby by sucking in another dosage of substance 32 into dosing chamber 30.

It is noted that chamber membrane 20 separates the actuating substance 18 from separation element 24. Separation element 24 thermally insulates substance 32 in dosing chamber 30 from actuating substance 18. Actuating chamber 16 is sealed, preferably by separation element 24, so that the actuating substance 18 is prevented from leaking into substance 32 in dosing chamber 30. More specifically, chamber membrane 20 encloses actuating chamber 16, and separation element 24, which is attached to membrane 20 before and after operation, prevents leakage of actuating substance 18 through chamber membrane 20 due to potential membrane permeability. Dosing chamber 30 and substance 32 are isolated from actuation substance 18 by a combination of chamber membrane 20, separation element 24 and substance-delivery membrane 28, thereby enhancing isolation and medical safety. Aperture 25 may be optionally ventilated through some vent passage 27 (FIG. 3A) to avoid pressure changes in aperture 25 during movements of separation element 24, and to drain any leakage of the actuation substance 18 or substance 32 if leaked through membrane 20 or 28 into aperture 25.

Alternatively, the thermal energy source 14 may be a cooling device (e.g., thermoelectric device) that cools actuating substance 18, which expands upon cooling.

Since delivery device 10 may be oriented in all kinds of orientations, including upside down, the actuating substance 18 may become distanced from thermal energy source 14. Accordingly, in one embodiment, actuating chamber 16 includes a maintaining element 52 (FIG. 3A) arranged to maintain actuating substance 18 in conductive thermal contact with thermal energy source 14 in any gravitational orientation. The maintaining element 52 may be, without limitation, carbon fibers, carbon cloth, capillary wires, rods or other slender elements, sponge members, electric charge device, and others.

Figure 4A:
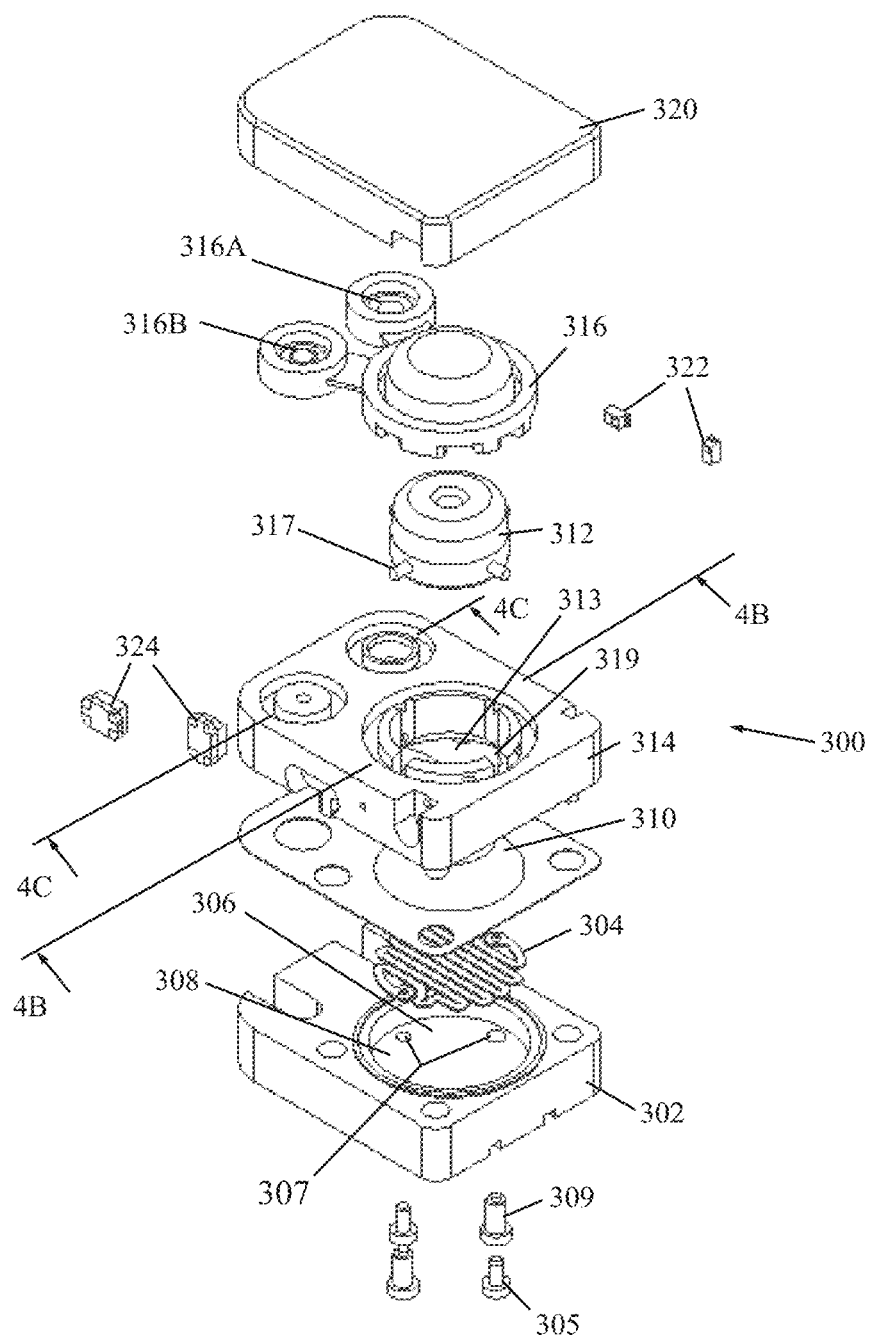
FIG. 4A is a simplified exploded illustration of a delivery device, constructed and operative in accordance with a non-limiting embodiment of the present invention.

Reference is now made to FIG. 4A, which illustrates a delivery device 300, constructed and operative in accordance with a non-limiting embodiment of the present invention.

Similarly to delivery device 10, delivery device 300 includes a base 302 on which is mounted a thermal energy source 304, such as but not limited to, one or more resistors or any other kind of resistive heating elements, or thermoelectric components. A controller (such as control logic circuitry or microprocessor and the like), sensors, wireless communications and other electronic components (all not shown for simplicity), for powering and controlling delivery device 300, may be mounted on base 302, as in delivery device 10. Contact posts 305 may be provided that are in electrical contact with thermal energy source 304 and which are in electrical contact with a power source for energizing the thermal energy source 304.

An actuating chamber 306 is formed in base 302 and contains an actuating substance 308, such as but not limited to, a fluid, e.g., water, alcohol, or a phase-change material with a high change in volume, e.g., inorganic salt hydrates, as before. It is noted, for example, that one of the electronic components in communication with the controller may be one or more temperature or pressure sensors 307, which may be useful for controlling the device and preventing overheating or over-pressurizing of the actuating substance 308. The actuating chamber 306 is covered by a chamber membrane 310 (which may be single layer or multi-layer) attached to base 302. The chamber membrane 310 may have a preformed shaped, such as but not limited to, a dome, as seen in the illustrated embodiment, or bellow or Belleville washer. Plugs 309 may be provided for filling and sealing actuating substance 308 in actuating chamber 306.

A separation element 312 rests against chamber membrane 310. Separation element 312 may be of a one-piece construction, or may be made of more than one piece. Separation element 312 sits in an aperture 313 formed in an intermediate member 314. Separation element 312 serves as the pushing apparatus that is arranged to push against a substance-delivery membrane 316 for pushing against and thereby dispensing a substance from a dosing chamber 320. Separation element 312 may include guiding members 317 to guide its travel in aperture 313, which are slidingly received in grooves 319 formed in member 314. Substance-delivery membrane 316 fluidly communicates with an inlet valve 316A and an exit valve 316B. Substance-delivery membrane 316, inlet valve 316A and exit valve 316B are all part of the same membrane layer. As before, dosing chamber 320 may have more than one compartment that contain substances for delivery (different or same substances).

As will be described further below with reference to FIGS. 10A-10B, optical sensors may be provided, which sense the position of the separation element 312. In the illustrated embodiment, the optical sensors include two light sources 322 (e.g., LEDs) which emit light beams that are detected by two light receivers 324. The light beams are positioned at two different places in the travel of separation element 312. In this manner, the optical sensors can easily detect the initial and final positions of separation element 312 (for example, to indicate that the drug has been properly dispensed).

Figure 4B:
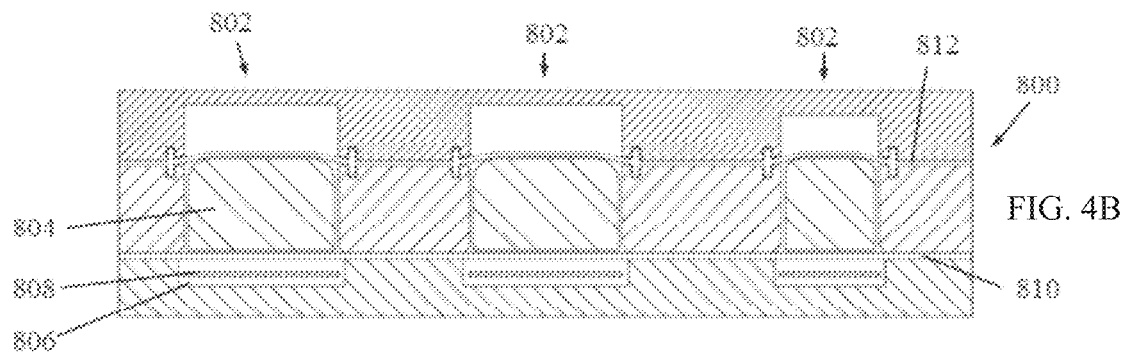
Figure 4C:
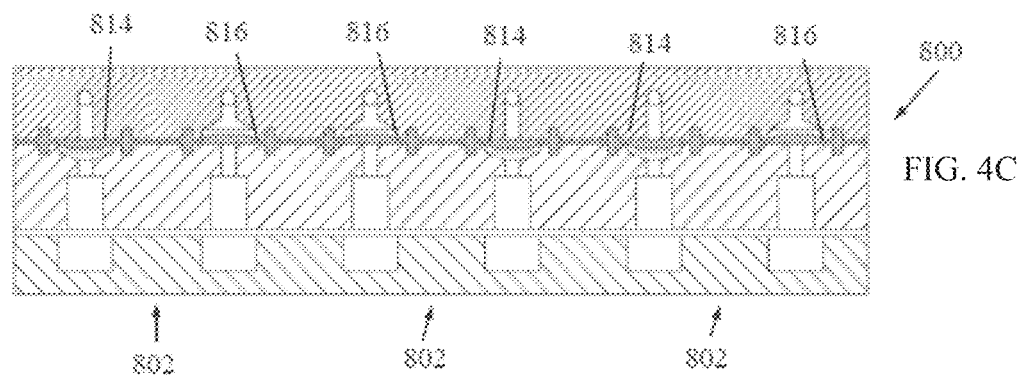

Reference is now made to FIGS. 4B and 4C, which illustrate another delivery device 800 that includes a plurality of dosing chambers 802. Each individual dosing chamber 802 may be constructed like the dosing chambers of FIG. 4A; FIGS. 4B and 4C are taken along lines 4B-4B and 4C-4C, respectively, in FIG. 4A. As seen in FIGS. 4B and 4C, the dosing chambers 802 may be of different sizes, but of course may alternatively be identical in size.

Each dosing chamber 802 has its own dedicated separation element 804 and actuation chamber 806 with thermal energy source 808. However, all the dosing chambers 802 share a common chamber membrane 810 and a common substance-delivery membrane 812. Membrane 812 also serves as the outlet and inlet valves 814 and 816, respectively, for each dosing chamber 802. It is noted that the membranes 810 and 812 each may have rims that are received in grooves in the device, which help achieve desired engineering properties of the membranes and valves, such as permissible stretching and positioning.

Figure 4D:
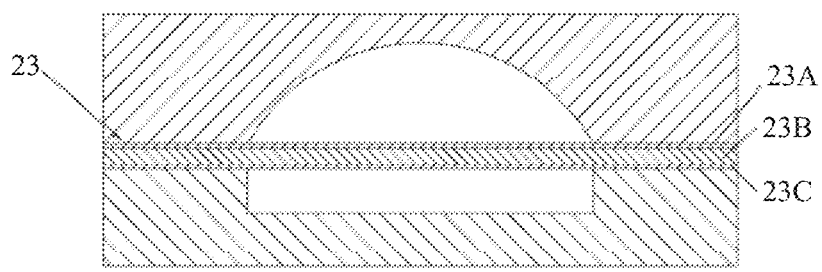
FIG. 4D is a simplified sectional illustration of a multi-layer membrane in accordance with a non-limiting embodiment of the present invention.

Reference is now made to FIG. 4D. The membranes 20 and 28 of the embodiment of FIG. 1A may be replaced by single multilayer membrane 23, including without limitation, a top layer 23A, intermediate layer 23B (which may serve as a thermal insulation layer) and a bottom layer 23C. This simplifies the construction as it eliminates the need for elements 20, 24, 25, 26, 27 and 28. The top layer 23A serves as the substance-delivery membrane (sealing the to-be-delivered substance in the dosing chamber), the intermediate layer 23B serves as the separator (mechanical and thermal isolation), and the bottom layer 23C serves as the chamber membrane 20 (overlying the actuating chamber containing the actuating substance), as in the previous embodiments. The top layer 23A and/or the bottom layer 23C may be a metal or metallized layer (such as by metal deposition of aluminum or silver metals or alloys) which achieves reduced or negligible permeability of the layer, and may also provide improved thermal insulation and other mechanical properties, such as reduced or negligible wrinkling or sagging.

Figures 1A, 1B:
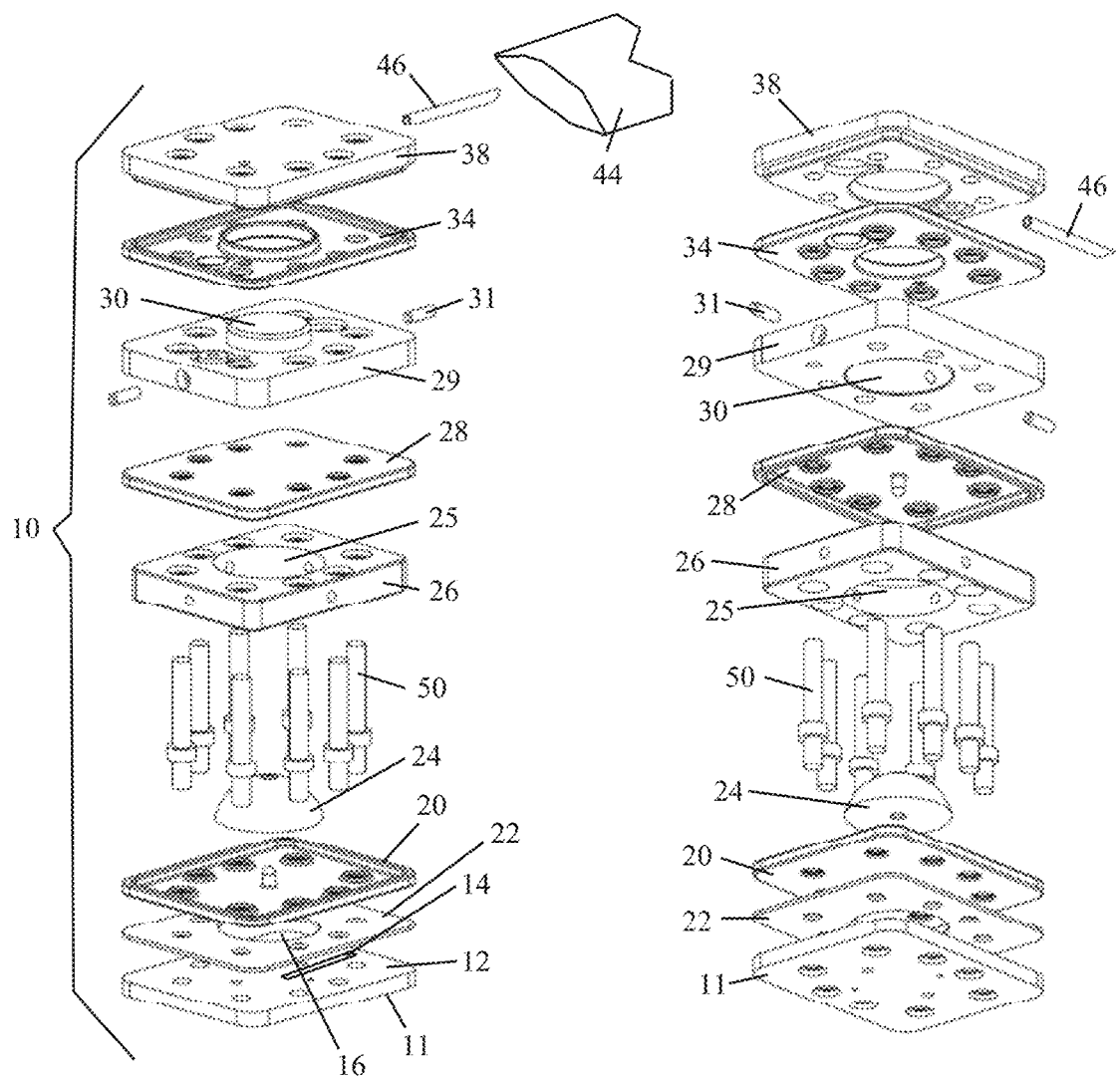
FIGS. 1A and 1B are simplified exploded illustrations of a delivery device, constructed and operative in accordance with a non-limiting embodiment of the present invention.
Figure 2:
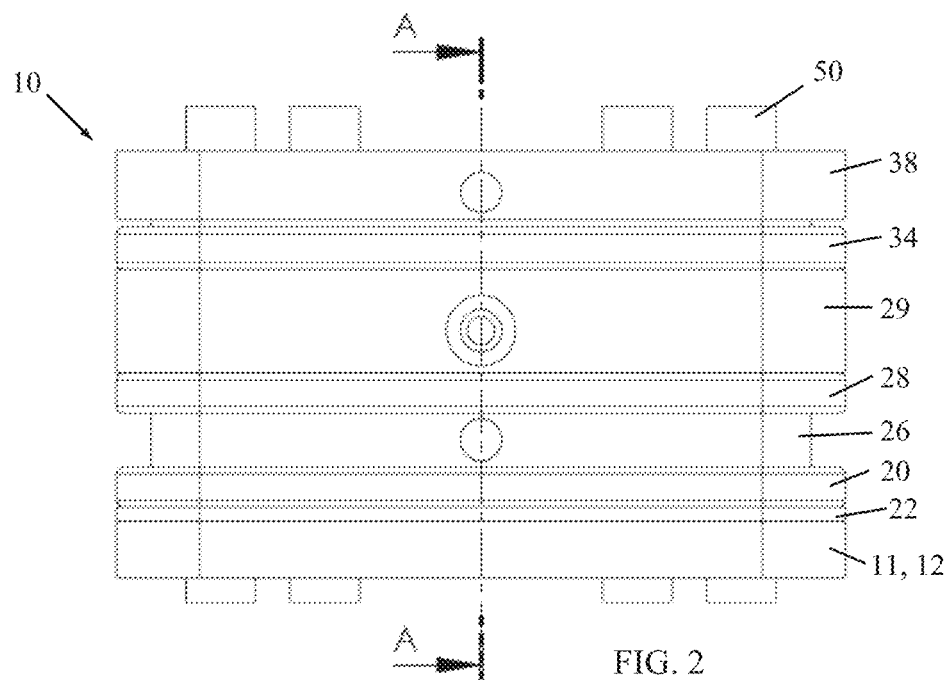
FIG. 2 is a simplified side-view illustration of the delivery device of FIGS. 1A-1B.

Of course, the membranes of the embodiments of FIGS. 1A and 4A, or any of the other embodiments of the invention, may be constructed as a variety of multilayer membranes.

Figure 5A:
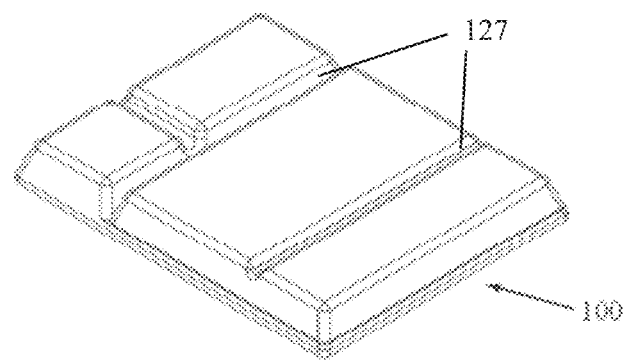
FIGS. 5A and 5B are simplified pictorial and exploded illustrations, respectively, of the delivery device, showing reusable and disposable portions, in accordance with a non-limiting embodiment of the present invention.
Figure 5B:
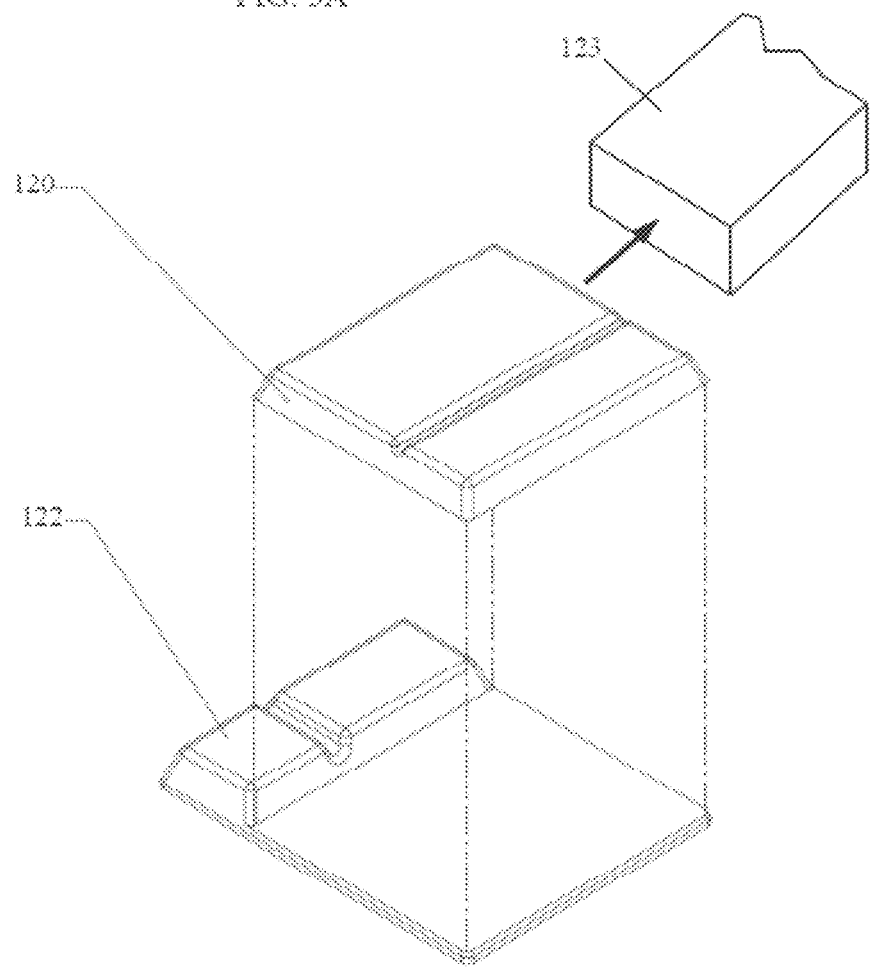

Reference is now made to FIGS. 5A and 5B, which illustrate that the entire device, including the dosing chamber, actuator and electronic components, may be encapsulated in a flexible, external housing 100. The device may be a patch (e.g., patch pump for drug delivery, such as but not limited to, insulin patch pump), which is attached to the skin of the user with adhesive or other suitable means. The device may be a disposable one piece product. Alternatively, in the illustrated embodiment, the device includes reusable 120 and disposable portions 122. For example, the dosing cell and/or battery may be on the reusable portion 120 or the disposable portion 122. As another example, the actuation part of the dosing cell may be reusable portion 120, whereas the dosing cell may be on the disposable portion 122, and the separation element placed between the two portions. The battery may be rechargeable or non-rechargeable.

Figure 5C:
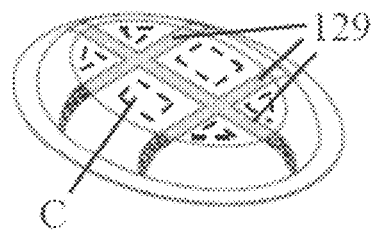
FIGS. 5C-5E are simplified pictorial, side-view before bending and side-view after bending views, respectively, of a delivery device, which may or may not have bending portions filled (fully or partially) with a resilient material, in accordance with a non-limiting embodiment of the present invention.
Figure 5D:
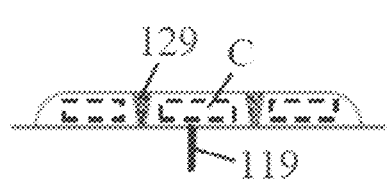
Figure 5E:
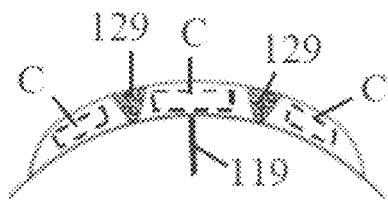
Figure 5F:
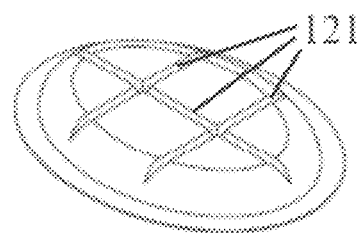
FIGS. 5F-5H are simplified pictorial, side-view before bending and side-view after bending views, respectively, of a delivery device with shallow bending lines, in accordance with a non-limiting embodiment of the present invention.
Figure 5G:
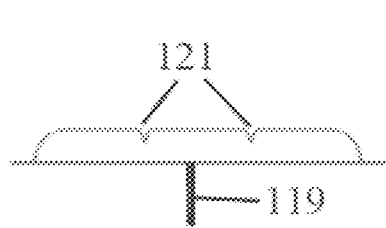
Figure 5H:
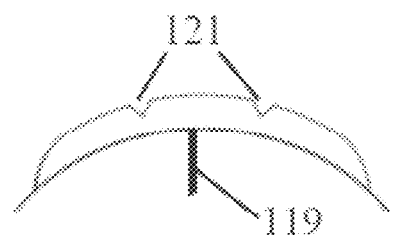

The reusable portion 120 may be mounted on a user control unit (e.g., personal diabetes manager that may include a blood glucose meter) 123, for example, simply for storing and ensuring that reusable portion 120 does not get lost, or for recharging the battery, or for data communication (e.g., uploading and downloading instructions and operational data). After operation and depletion of the battery, reusable portion 120 may be detached from the disposable portion 122 and attached to user control unit 123 for recharging for later reuse. Meanwhile another reusable portion 120 can be attached to a new disposable portion 122 and put into operation on the user's skin. As seen in FIGS. 5A and 5B, the components of the device are separated by bending lines 127. The position of the bending lines 127 and/or the components of the device can be designed to achieve different bending modes (e.g., allowing easier bending in certain directions but different—for example, more difficult—bending in other directions). Additionally or alternatively, different bending modes and properties can be achieved by using a combination of different materials with different hardnesses or other mechanical properties. One example is shown in FIGS. 5C-5E, which has bending portions 129 filled (fully or partially) with a resilient material which may be different than the rest of the device or the same material but made with a different hardness. As seen in FIG. 5E, the bending portion may stretch so that it "vees" outwards more than when not stretched (FIG. 5D). Alternatively, there may be no bending portions 129 and the encapsulated device bends in accordance with the placement of the components C, which determine the different bending possibilities of the device. The components C may be flexible, semi-rigid or rigid, e.g., drug reservoir, battery, dosing device and others. Another example is shown in FIGS. 5F-5H, in which the components of the device are separated by shallow bending lines 121. In the embodiments of FIGS. 5C-5H, a cannula 119 protrudes from the device for drug delivery (as explained elsewhere a needle may first puncture the user's skin and then be retracted, leaving the cannula in place for drug delivery).

A further example of the possible combinations of reusable and disposable portions of a device 100A is shown in FIGS. 5I-5J. The reusable portion 120 may be inserted in a socket 123A formed in user control unit 123 (such as, without limitation, a smart phone), for example, simply for storing and ensuring that reusable portion 120 does not get lost, or for recharging the battery or for data communication.

A further example of the possible combinations of reusable and disposable portions of the device is shown in FIG. 5K. The reusable portion 120 may be inserted in a socket 401 formed in a protective cover 402 (which may be made of a flexible elastic material) of a smart phone or personal diabetes manager 403 which serves as the user control unit. Socket 401 has pins, tabs or other connectors for connecting to corresponding connections in the reusable electronic module (i.e., reusable portion) 120. The connectors of socket 401 may in wired communication with a port 404. A smartphone charging/communication cable 405 may connect to port 404, either directly or via an intermediate adaptor (not shown). Port 404 thus serves as a communication and charging connector, for example, for recharging the battery of reusable portion 120 or for communicating with reusable portion 120. Port 404 may be molded or otherwise assembled together with protective cover 402.

Figure 6A:
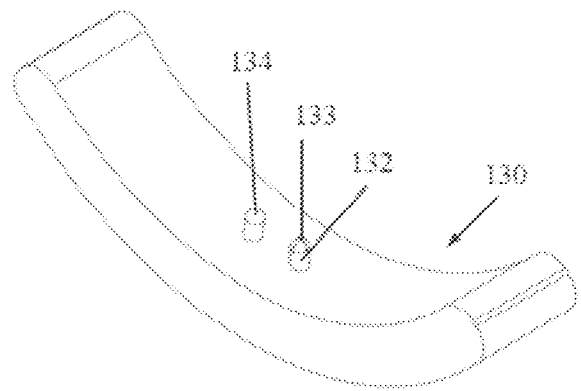
FIGS. 6A, 6B and 6C are simplified external pictorial, internal pictorial and sectional illustrations, respectively, of a delivery device for use as a collar, constructed and operative in accordance with a non-limiting embodiment of the present invention.
Figure 6B:
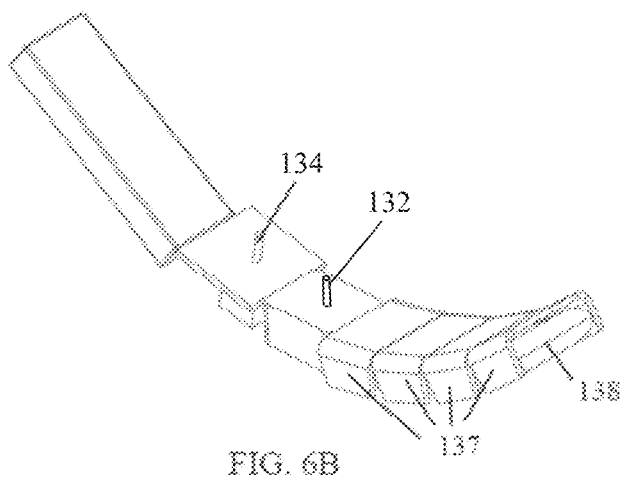
Figure 6C:
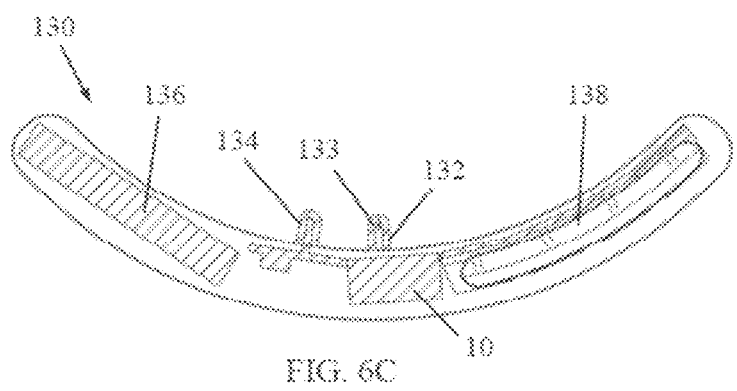

Reference is now made to FIGS. 6A-6C, which illustrate a delivery device 130 for use as a collar, constructed and operative in accordance with a non-limiting embodiment of the present invention. This is particularly useful for pets, such as dogs or cats. Alternatively, the device can be in the form of a harness or neck strap, for use with farm animals, such as horse, cattle, sheep, goats, etc. Alternatively, the device can be used for humans. The term "collar device" encompasses a standalone collar and a collar accessory which is attached to a collar.

As seen in FIG. 6C, delivery device 130 includes one or more delivery devices 10, which are used to deliver a substance through a dosing probe 132, which extends to the skin of the animal. The entire delivery device 130, which includes any of the actuators and controllers of any of the other embodiments, may be encapsulated in a flexible, external housing (such as by over-casting or molding in a suitable polymeric material. This achieves a flexible feel, robust mechanical properties and can be made with a simple, low-cost production.

Dosing probe 132 is preferably flexible and bendable. A seal or valve 133 is positioned at or near the tip of probe 132 to avoid congelation/drying of the substance to be administered. A skin contact sensor 134 is provided for sensing that the collar is properly positioned on the animal so that the substance is administered only when the collar is on the animal. "Properly positioned" means the collar is touching the fur or skin of the animal and probe 132 is directed towards the fur or skin of the animal. Sensor 134 may be a temperature sensor (e.g., thermistor) that senses contact with the skin by means of sensing the skin temperature. This also provides a safety feature, by discriminately sensing normally higher animal temperatures (which are typically higher than normal human body temperature). Alternatively, the sensor can be a proximity sensor, such as a capacitance sensor. A battery 136 is provided in the collar. As seen in FIG. 6B, the collar may include flexible, jointed portions 137 that protect the device 10 from external force/pressure, yet can be flexed and bent to best suit the collar shape and the animal's neck.

Figure 6E:
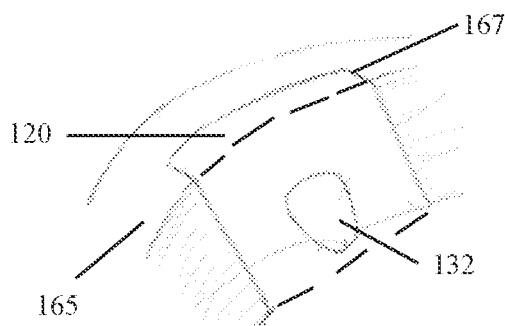
FIG. 6E is a simplified pictorial illustration of a delivery device with a socket for receiving a disposable dosing portion, in accordance with a non-limiting embodiment of the present invention.
Figure 6D:
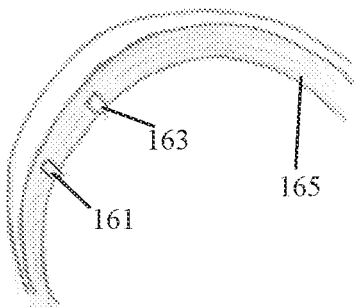
FIG. 6D is a simplified pictorial illustration of a delivery device which is a standalone, one-piece collar, in accordance with a non-limiting embodiment of the present invention.

The device may be attached to an existing collar (as in FIGS. 6A-6C), or alternatively may be provided as an integral part of the collar, that is, a standalone, one-piece collar, as seen in FIG. 6D. Optional dosing probes and/or sensors 161 and 163 can sense proximity or attachment of the collar 165 to the animal, or can sense if the collar is open to ensure safe operation and avoid drug delivery once the collar is removed from the animal. The device can be used, for example, to deliver multiple drugs (see embodiments of FIG. 8) for combating multiple parasites (e.g., fleas, ticks, heartworms, etc.).

As seen in FIG. 6E, instead of a one-piece construction, a socket 167 can be formed in the collar 165 for receiving a disposable dosing portion 120, which may be made like any of the disposable units described throughout the specification, such as disposable unit 120, and which may contain the drug capsule, dosing cell, battery or any other components, and which may have a dosing probe 132.

Figure 6F:
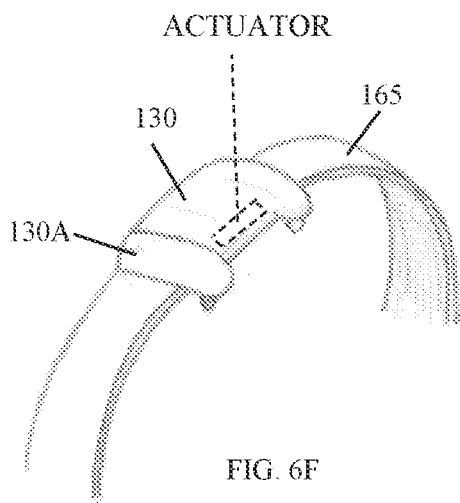
FIGS. 6F and 6G are simplified pictorial illustrations of delivery devices, in which a dosing portion of the delivery device may be a disposable part mounted above a collar frame (FIG. 6F) or below the collar frame (FIG. 6G)
Figure 6G:
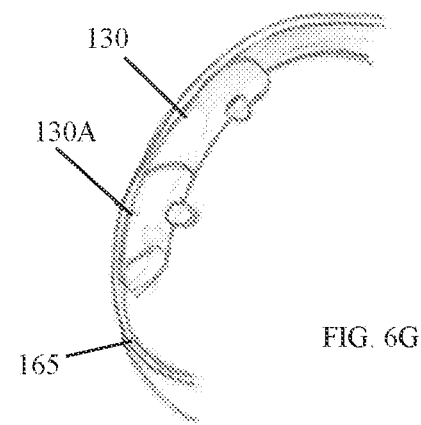

As seen in FIGS. 6F and 6G, the collar can have the dosing portion of the delivery device 130 as a disposable part 130A mounted on the collar frame 165 (above the collar frame as in FIG. 6F or below as in FIG. 6G). Alternatively, part 130A is not separate from device 130; rather they are one unit which is either disposable or reusable.

Figure 6H:
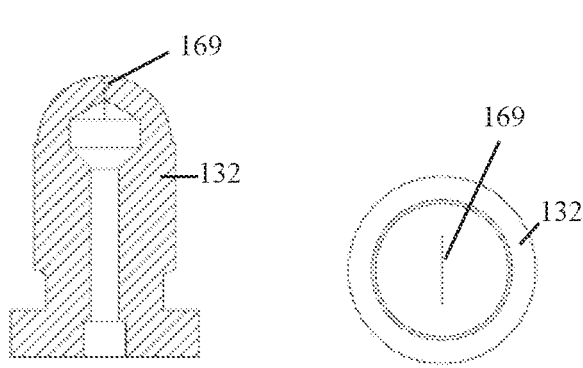
FIGS. 6H-6J are simplified sectional, top-view and side-view illustrations, respectively, of a dosing probe formed with a distal exit slit, in accordance with a non-limiting embodiment of the present invention.
Figure 6I:
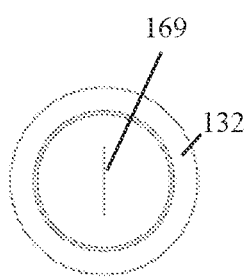
Figure 6J:
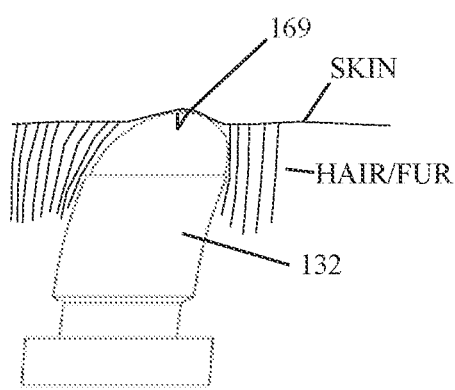

As seen in FIGS. 6H-6J, the dosing probe 132 may be formed with a distal exit slit 169 (e.g., like a duck bill). The flexible dosing probe 132 with its exit slit 169 can prevent clogging of dosing probe 132, because they prevent ingress of outside air, and if a clog forms, the dosing probe 132 and slit 169 extend/expand to eject the clogged particle. The dosing probe 132 can bend upon pressing against the fur or skin of the animal, and this also helps to release any clogs.

Figure 7A:
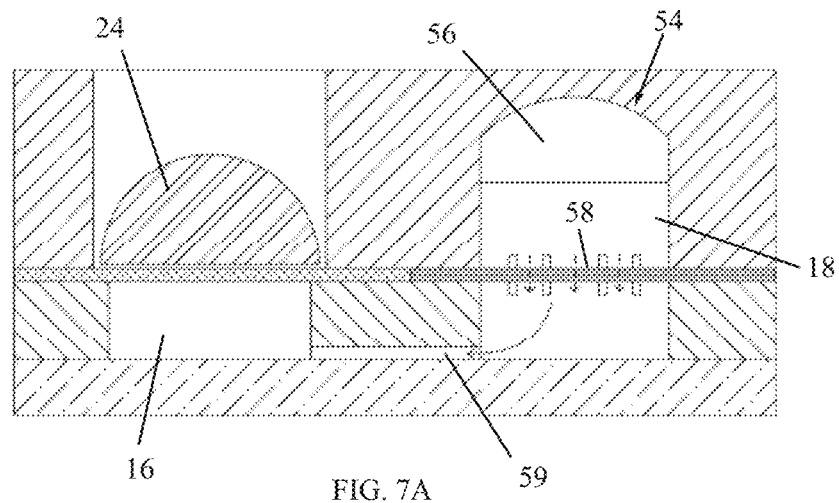
FIG. 7A is a simplified illustration of a filling device, constructed and operative in accordance with a non-limiting embodiment of the present invention.

In order to maintain a necessary amount of actuating substance 18 in actuating chamber 16, the delivery device 10 may further include a filling device 54 operatively connected to actuating chamber 16. In one embodiment, shown in FIG. 7A, filling device 54 includes a reservoir 56 at least partially filled with actuating substance 18, and pressurized at low pressure. Actuating substance 18 in reservoir 56 is nominally separated from actuating chamber 16 by a membrane 58. However, membrane 58 is somewhat permeable to actuation substance 18 so that an osmotic pressure difference (higher pressure on the reservoir side of membrane 58) will causes a very slow passage of actuation substance 18 through membrane 58 over a long period of time. Thus, if actuating substance 18 leaks out of actuating chamber 16 for any reason, this causes a drop in pressure in actuating chamber 16. Since reservoir 56 is partially pressurized, the difference in pressure will cause a slow passage of actuation substance 18 from reservoir 56 through membrane 58 and via a conduit 59 into chamber 16, thereby replenishing actuating chamber 16 with actuating substance 18. Reservoir membrane 58 thus serves as one-way valve at a very slow rate and over long period of time.

Figure 7B:
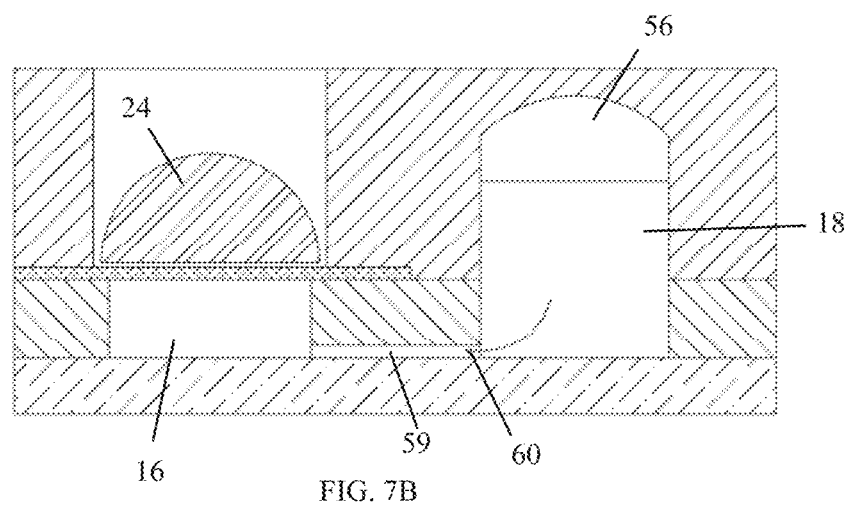
FIG. 7B is a simplified illustration of a filling device, constructed and operative in accordance with another non-limiting embodiment of the present invention.

In another embodiment, shown in FIG. 7B, the actuating substance 18 in reservoir 56 flows to actuating chamber 16 via conduit 59 and a directional valve 60 (e.g., one-way valve).

Figure 8:
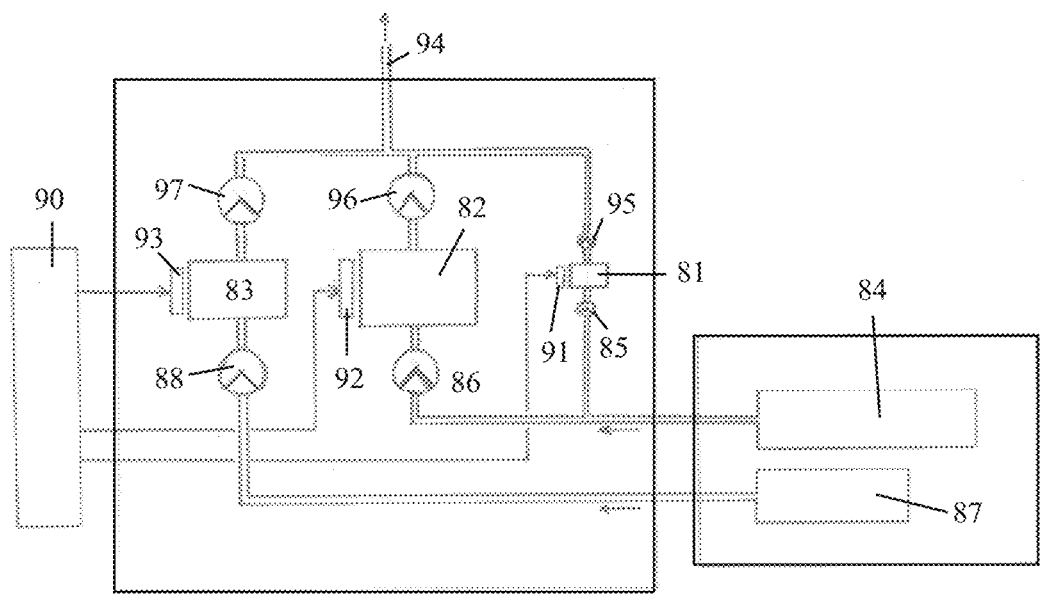
FIG. 8 is a simplified illustration of a delivery device with multiple dosing chambers, constructed and operative in accordance with a non-limiting embodiment of the present invention.

Reference is now made to FIG. 8. In this embodiment, the delivery device includes a plurality of dosing chambers, for example, dosing chambers 81, 82 and 83 (any number is within the scope of the invention). In the illustrated embodiment, a reservoir 84 of a first substance (such as, but not limited to, insulin) is connected to dosing chambers 81 and 82 via one-way valves 85 and 86, respectively. A reservoir 87 of a second substance (such as, but not limited to, GLP-1 [glucagon-like peptide-1] analogs) is connected to dosing chamber 83 via a one-way valve 88. In other embodiments, each of the dosing chambers may contain a different substance to be delivered. In the illustrated embodiment, dosing chambers 81, 82 and 83 are of different sizes (81 being the smallest and 82 the largest. For example, without limitation, chamber 81 may be used for a basal dosage of insulin (such as 0.5 µl), whereas chamber 82 may be used for a bolus dosage (such as 10 µl).

In the illustrated embodiment, each dosing chamber has its own dedicated separation element and/or actuation chamber, collectively labeled 91, 92 and 93. In another embodiment, there is a common separation element and/or actuation chamber for all of the dosing chambers. A controller 90 controls operation of the actuation chambers.

It is noted that in any of the embodiments of the invention, communication with the controller may be wireless or through the Internet or with any kind of suitable communication means.

In the illustrated embodiment, there is a common outlet 94 for all of the dosing chambers via one-way valves 95, 96 and 97, respectively. Alternatively, separate outlets may be provided. Alternatively, a common inlet may be used for all of the dosing chambers.

Figure 9:
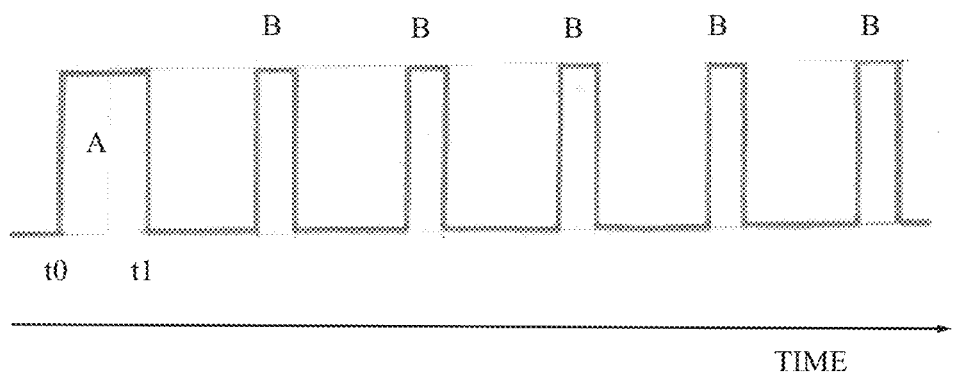
FIG. 9 is a simplified graphical illustration of actuation pulses for the thermal energy source to heat the actuating substance, in accordance with a non-limiting embodiment of the present invention.

Controller 90 may be used to provide a variety of dosage plans, depending on the patient (human or animal) and the substances being administered. In one non-limiting example, dosing chamber 81 may be used to administer a basal amount of insulin, at any rate of dosage amount per time (e.g., discrete small dosages of insulin at set time intervals; the amount, time interval and length of time the dosages are given can be modified). Before meals, dosing chamber 82 may be used to administer a bolus of insulin, such as two boluses of 10 µl of insulin plus a few dosages of 0.5 µl from chamber 81. Reservoir 87 and dosing cell 83 may be used for providing boluses of GLP-1 before meals. Alternatively, they may be used for dosing glucagon in emergency cases of hypoglycemia. Reference is now made to FIG. 9, which illustrates an example of actuation pulses for thermal energy source 14 to heat actuating substance 18, as controlled by controller 90 (FIG. 8). The number of actuation pulses may be determined by the size and number of the dosing chambers. Initially, a relatively large amount of energy is required to heat the actuating substance to vapor, as indicated by initial pulse A from time t0 (membrane at initial, unexpanded state; full chamber) to time t1 (membrane at fully expanded state; empty chamber). The device may include sensors (examples described below) that sense the full or empty state of the dosing chamber, or the position of the chamber membrane and/or the separation element. This may help save on the energy and time needed to heat the actuating substance for the next dosage, because the controller knows when the actuating substance has cooled enough so that the chamber membrane has gone back to its initial state (e.g., near the bottom of the actuating chamber) and can start reheating the actuating substance, which is near its vapor temperature, before the actuating substance has cooled down unnecessarily. Thus, the subsequent energy pulses B may be significantly shorter and of less magnitude than the initial pulse A. The heating times may be in the range of milliseconds to several seconds, for example.

Figure 9A:
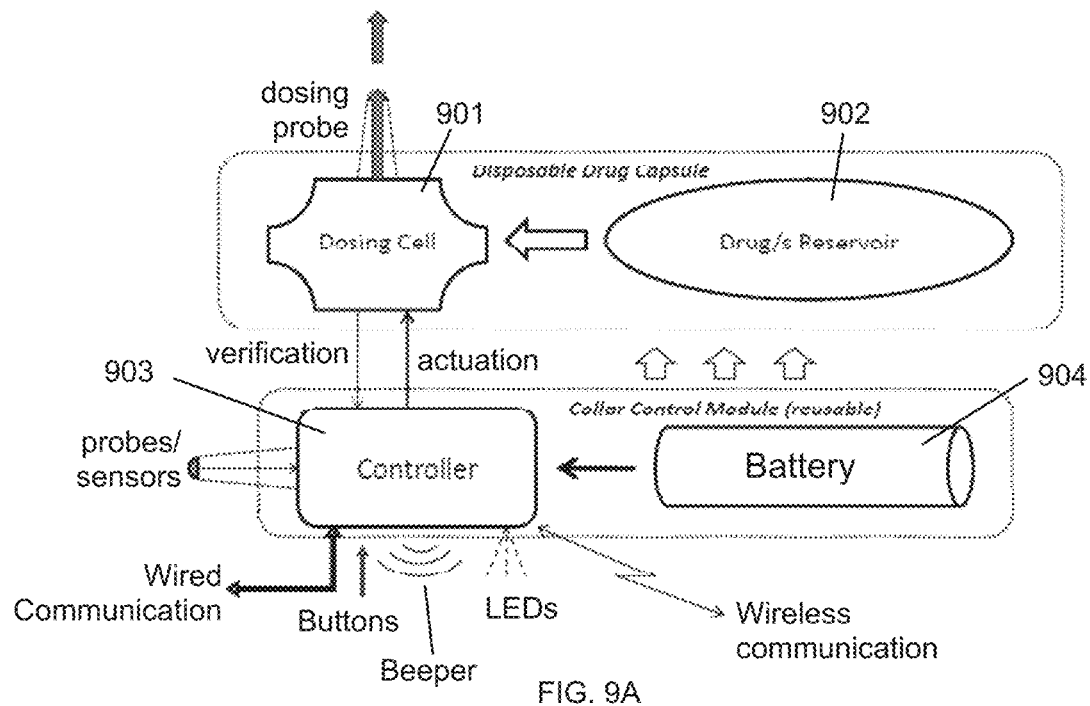
FIGS. 9A, 9B and 9C are simplified block diagrams of non-limiting methods of using drug delivery devices of the invention.
Figure 9B:
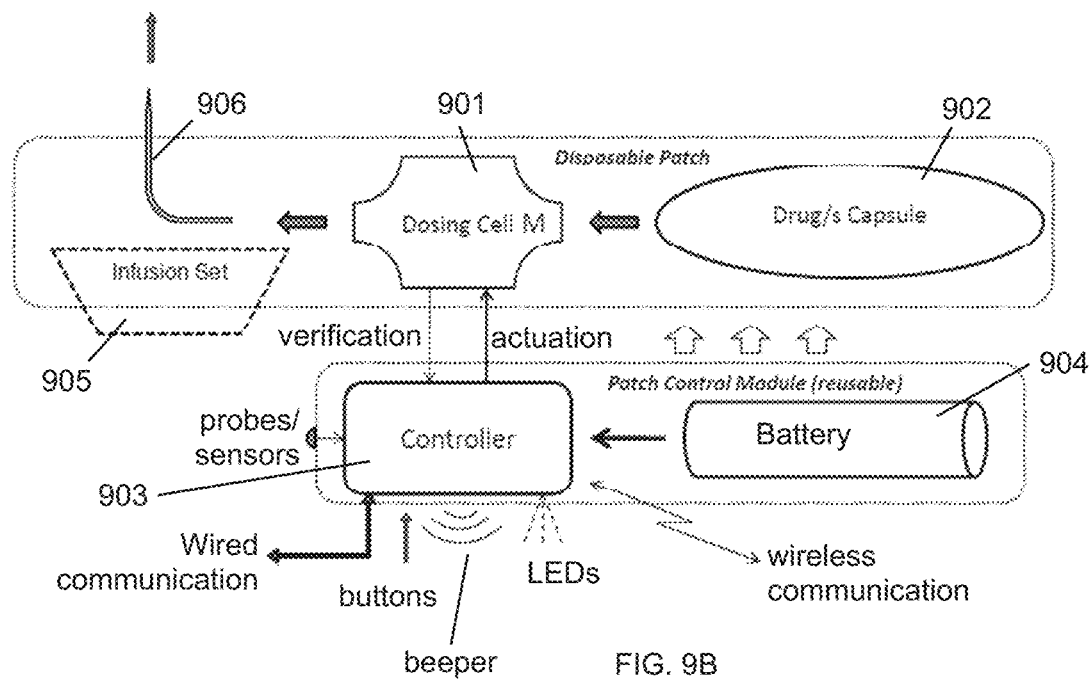
Figure 9C:
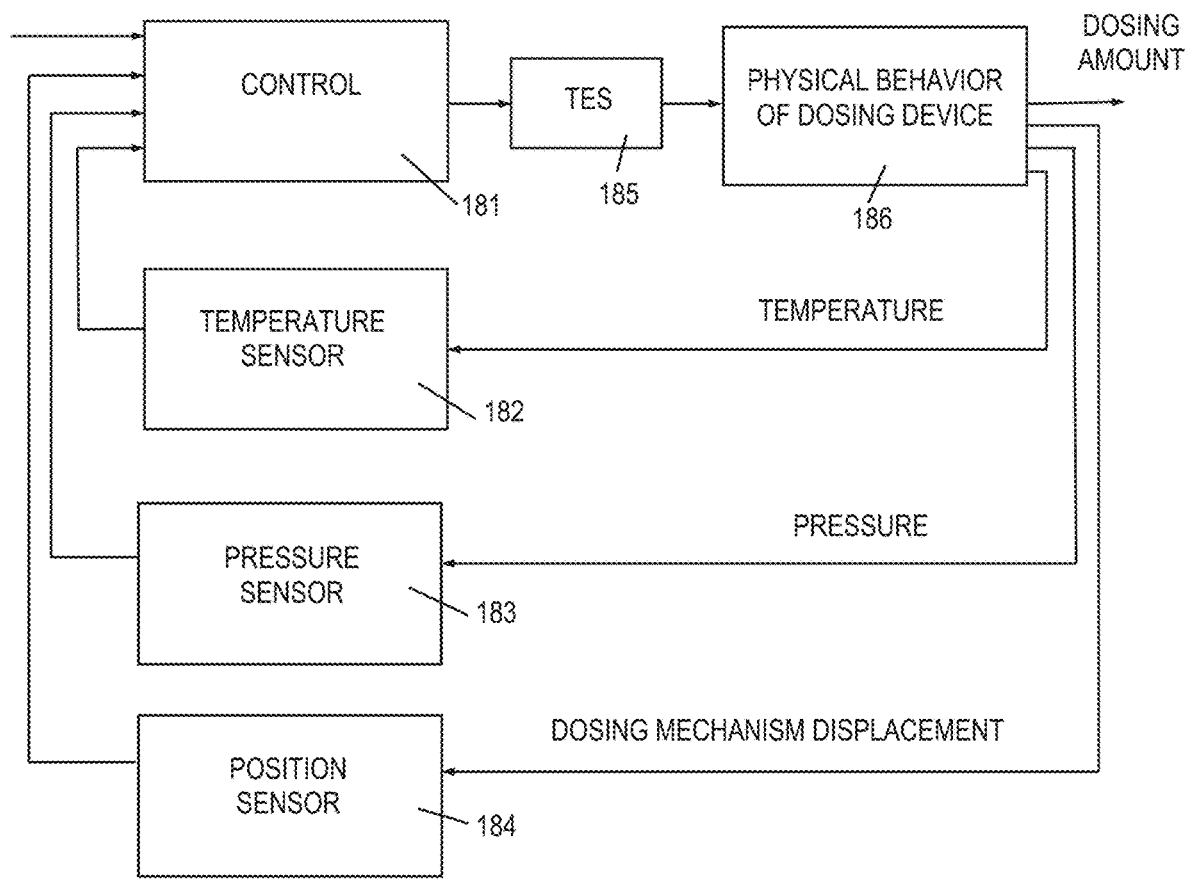

Reference is now made to FIGS. 9A, 9B and 9C, which illustrate non-limiting methods of using drug delivery devices of the invention. FIG. 9A illustrates using the collar device of the invention for animals (or humans), such as that of FIGS. 6A-6C. The collar device may be configured as a reusable device with one or more disposable drug capsules, which include the dosing cell 901 and drug reservoir(s) 902. Alternatively the device may be a fully disposable one-piece device. The device may be provided as a standalone collar or an accessory attached to the pet's collar. The device has a control module which includes a controller 903 and battery 904. The controller provides dosing actuation and verification. The device can operate via wireless communication with a smartphone, Wi-Fi or any other suitable communication device. Various sensors may be provided, such as without limitation, body temperature sensors, probe or other animal sensors, etc.

FIG. 9B illustrates using an insulin device of the invention, such as that of FIG. 8. The device may be configured as a disposable patch, which includes the dosing cell 901 and drug capsule(s) 902 (e.g., insulin, GLP-1, glucagon) and infusion set 905 (including a needle which may be removed after infusion, and a cannula 906). The device has a control module which includes a controller 903 and battery 904. The controller provides dosing actuation and verification. The device can operate via wireless communication with a personal diabetes manager, smartphone, WiFi or any other suitable communication device. Various sensors may be provided, such as without limitation, body temperature sensors or other body sensors, etc.

FIG. 9C illustrates a dosing control system, which may operate in a closed or open control loop, and which may be used in any of the embodiments of the invention. The control system may include, without limitation, a control module 181, one or more temperature sensors 182, one or more pressure sensors 183, and one or more position sensors 184. The control module 181 can control electrical power to various components of the delivery device, such as but not limited to, the thermal energy source 185 (e.g., heating element), actuators and others. The control module 181 may control operation in accordance with a physical behavior model 186 of the dispensing device or any operational portion of the device controlled by the dosing control system. The physical behavior includes, without limitation, thermodynamic, mechanical, and/or chemical behavior and other behaviors. Accordingly, in one embodiment, by processing all the sensed and/or stored information, the control module 181 controls the dosage provided to the user in a closed control loop with feedback. In another embodiment, the control module 181 controls the dosage provided to the user in an open control loop, without taking into account sensed information for feedback. For example, the control module 181 can provide a series of operating electrical pulses with a predetermined time duration and magnitude.

Figure 9D:
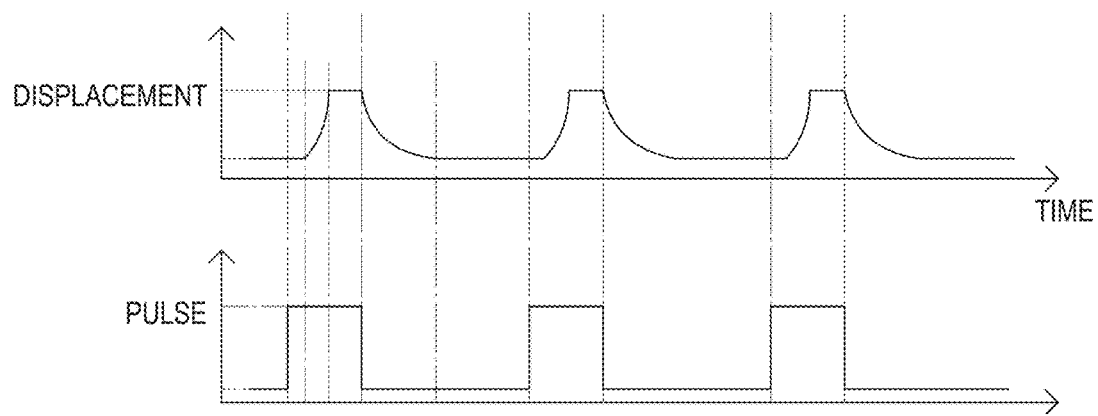
FIGS. 9D-9F are simplified graphical illustrations of different pulse trains for operating the delivery devices of the invention.
Figure 9E:
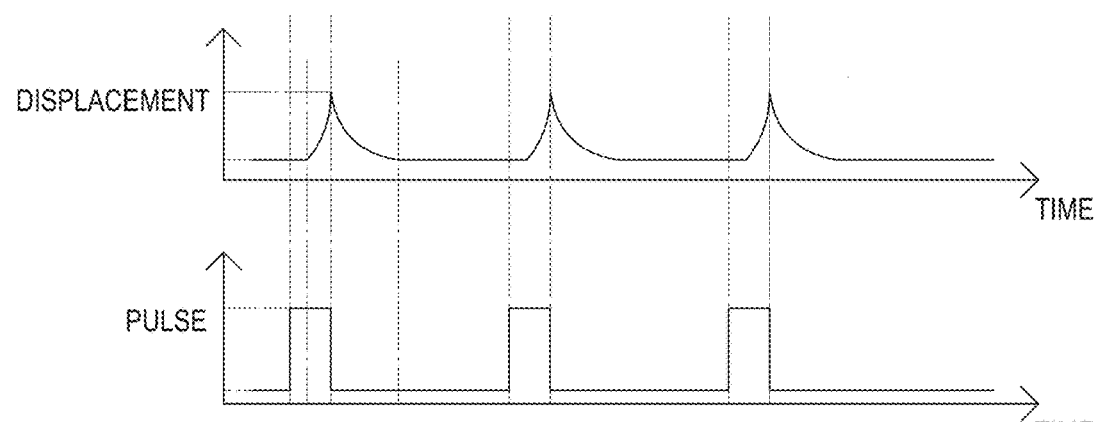
Figure 9F:
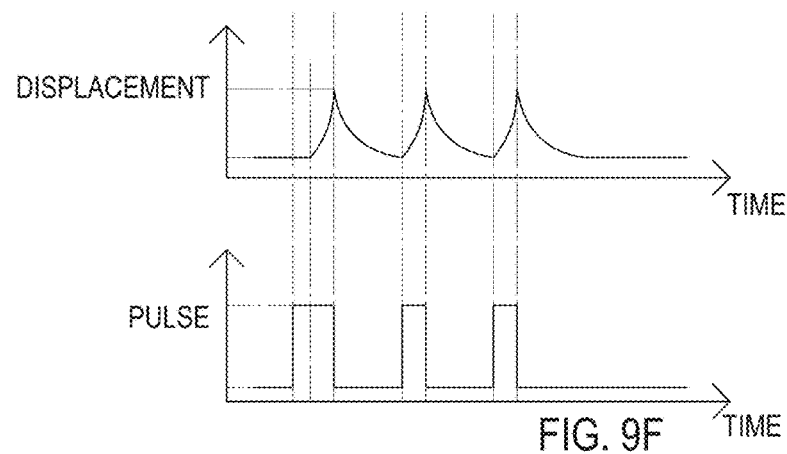

Examples are shown in FIGS. 9D-9F. The amount of substance administered by the dosing device is related to the number of pulses in a pulse train that heat the actuating substance to cause the dosing mechanism to administer the substance from the dosing cell. The magnitude and duration of the pulse train, as well as the gaps between the pulses (i.e., the duration of no energy between the pulses), determines the dosage and energy efficiency characteristics. The graphs show the displacement of the dosing mechanism (e.g., any of the membranes and/or separator) vs. time and the pulses vs. time. It is noted that the dosing mechanism travels between two limits, e.g., a starting position and finishing position.

In FIG. 9D, pulses are provided at a predetermined time duration with gaps of no energy between them (open loop). Thus, the pulses are provided at predetermined time periods and the pulse duration is also predetermined.

In FIG. 9E, position sensor data for the finishing position is used in a feedback loop to control the pulses. When the dosing mechanism has reached its finishing position, the pulse is stopped. Thus, the pulses are provided at predetermined time periods, but the pulse duration is not predetermined, rather it ends when the dosing mechanism has reached its finishing position. This conserves energy as opposed to FIG. 9D, because the pulses last shorter. It also saves overheating and over-pressurizing of the device.

In FIG. 9F, position sensor data for the starting and finishing positions is used in a feedback loop to control the pulses. When the dosing mechanism has reached its finishing position, the pulse is stopped. When the dosing mechanism has returned to its starting position, the next pulse starts. Thus, the pulses are not provided at predetermined time periods, rather the pulse ends when the dosing mechanism has reached its finishing position and the next pulse starts upon the dosing mechanism returning to its starting position. This conserves energy even more energy as opposed to FIG. 9E, because the substance has not fully cooled between pulses, but just cooled enough to reach the starting position.

Figure 9G:
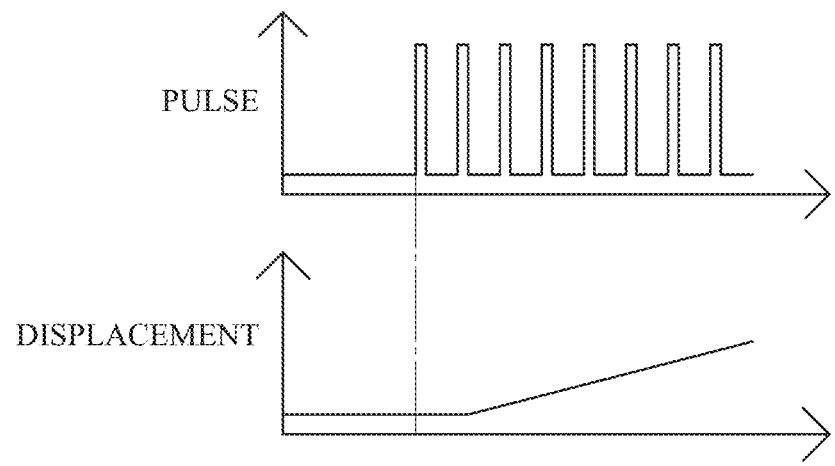
FIGS. 9G and 9H are simplified graphical illustrations of PWM pulse trains for operating the delivery devices of the invention.
Figure 9H:
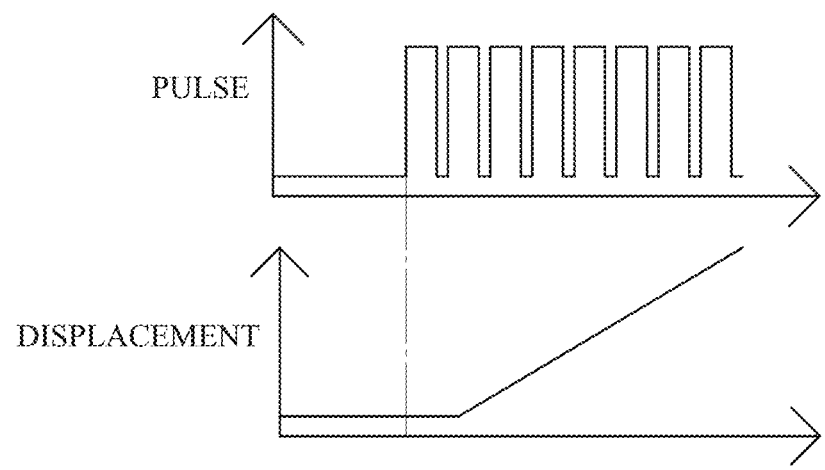

Other examples of controlling the pulses for operation of the device are shown in FIGS. 9G and 9H. In these examples, pulse-width modulation or pulse-duration modulation (PWM) is used to determine the width or duration of the pulse based on modulation signals. The PWM duty cycle is equal to (time on)/(time on+time off).

In the systems of FIGS. 9D-9F, each pulse is a step function which is basically immediately input at a constant magnitude to cause displacement of the dosing mechanism. By using PWM, each individual pulse of FIGS. 9D-9F is divided into shorter pulses and the frequency of these pulses can be controlled so that the input to the dosing mechanism is not a step function but rather a gradual increase, as seen in FIGS. 9G and 9H, or other mathematical functions. By combining PWM with feedback sensors, the control system can provide very controlled displacement of the dosing mechanism to suit any dosing rate and quantity according to desired dosing protocols.

The control system can immediately sense different dosing problems. For example, if some clog has formed (such as in the cannula, needle or dosing cell) the control system will detect that the finishing position of the pushing apparatus or substance-delivery membrane has not been reached within the defined time. The control system recognizes this delay, i.e., longer dosing time, as the presence of a clog or other kind of obstruction. Conversely, if there is some leak, the control system will detect that the finishing position of the pushing apparatus or substance-delivery membrane has been reached before the defined time due to a reduced or lack of resistance to the movement. The control system recognizes this shorter dosing time as the presence of a leak.

The control system can combine the above with temperature and/or pressure sensors to improve the accurate assessment of dosing time and behavior to improve the sensitivity of sensing clogs and leaks. The displacement, temperature and pressure sensors are examples of sensors that sense a rate of delivering the substance from the dosing chamber, and other suitable sensors can also be used. The control system can provide alarms of clogging or leaking or other abnormal dosing behavior.

Figure 10A:
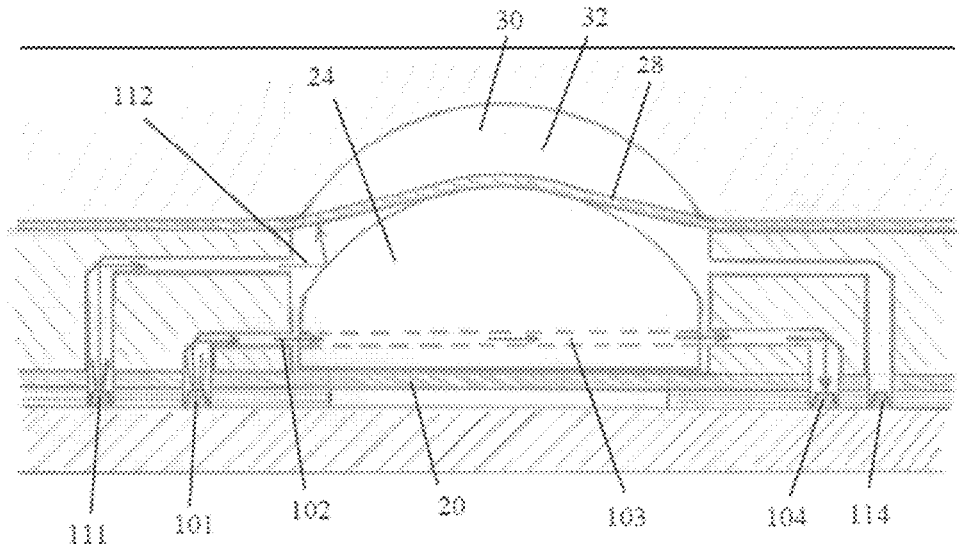
FIGS. 10A and 10B are simplified illustrations of optical sensors that sense the position of the separation element, in accordance with a non-limiting embodiment of the present invention, respectively with the separation element at initial and final positions.
Figure 10B:
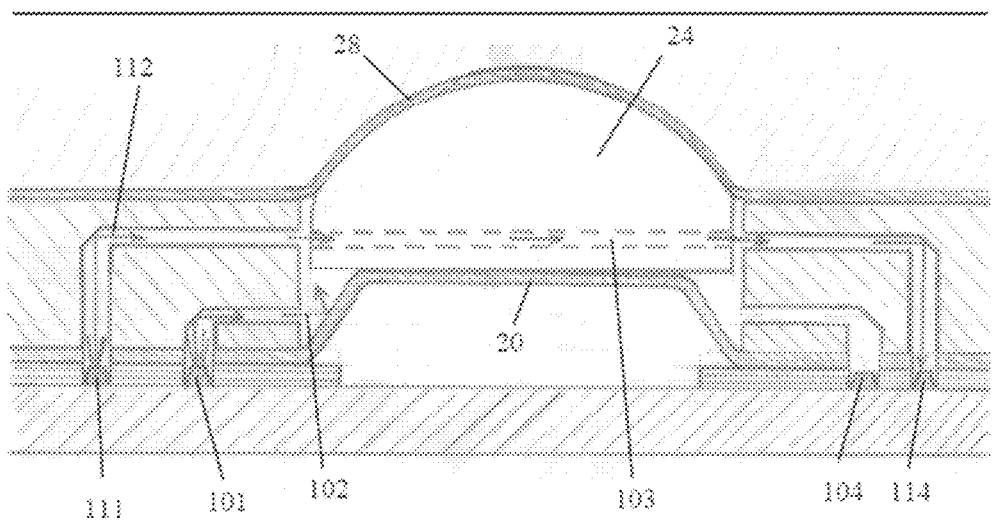

Reference is now made to FIGS. 10A-10B, which illustrate optical sensors that sense the position of the separation element 24. In the illustrated embodiment, in FIG. 10A, separation element 24 is at the initial position, wherein chamber membrane 20 has not yet expanded and substance-delivery membrane 28 has not yet been forced against the substance 32 in chamber 30. A first light source 101 (e.g., LED) emits a first light beam 102 through a passage 103 formed in separation element 24. The first light beam 102 is detected afterwards by a first light receiver 104. Similarly, a second light source 111 emits a second light beam 112. In the position of FIG. 10A, second light beam 112 is reflected off separation element 24. After separation element 24 has moved to the final position, shown in FIG. 10B (in this position, all of the substance 32 has been delivered from chamber 30), the second light beam 112 now can pass through passage 103 and is detected by a second light receiver 114. In the final position, the first light beam 102 is reflected off chamber membrane 20. In this manner, the optical sensors can easily detect the initial and final positions of separation element 24 (for example, to indicate that the drug has been properly dispensed).

Figure 10C:
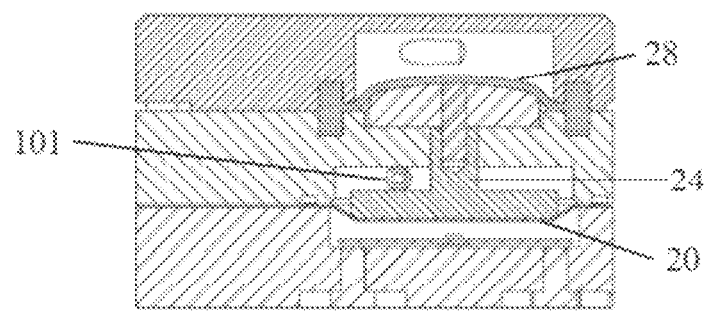
FIGS. 10C-10E are simplified illustrations of use of the optical sensor, in accordance with a non-limiting embodiment of the present invention, wherein the light source is at first unobstructed by the separation element (FIG. 10C), then gradually obstructed as the separation element rises (FIG. 10D) and then fully obstructed when the separation element moves to its maximum level (FIG. 10E)
Figure 10D:
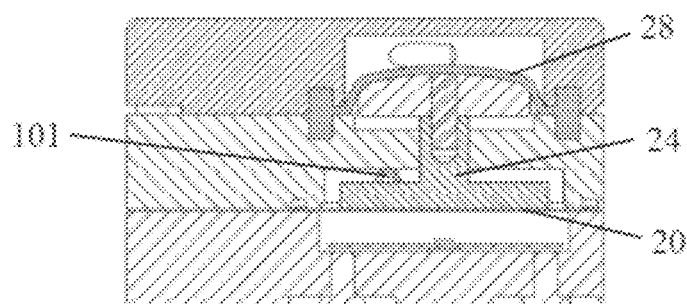
Figure 10E:
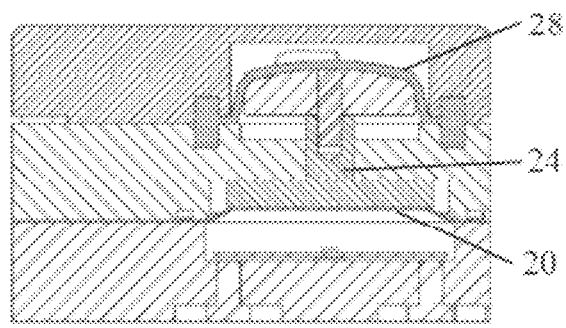

The sensors can be implemented in other ways as well, such as but not limited to, only one light receiver, or only one LED in a variety of operational logics. For example, one light receiver may have a larger viewing port or window and serve as an analog sensor, that is, it views the rising and setting of the separation element or other moving portion of the assembly. An example of such an arrangement is shown in FIGS. 10C-10E, which shows the light source 322 of the embodiment of FIG. 4A. Light source 322 is at first unobstructed by the separation element 312 (FIG. 10C), then gradually obstructed as the separation element 312 rises (FIG. 10D) and then fully obstructed when the separation element 312 rises to its maximum level (FIG. 10E). This arrangement allows various precise dosing rates profiles in a closed loop control as previously explained.

Other types of sensors, such as but not limited to, electrical contacts or capacitance proximity sensors, may be used instead of the optical sensors.

Figure 11A:
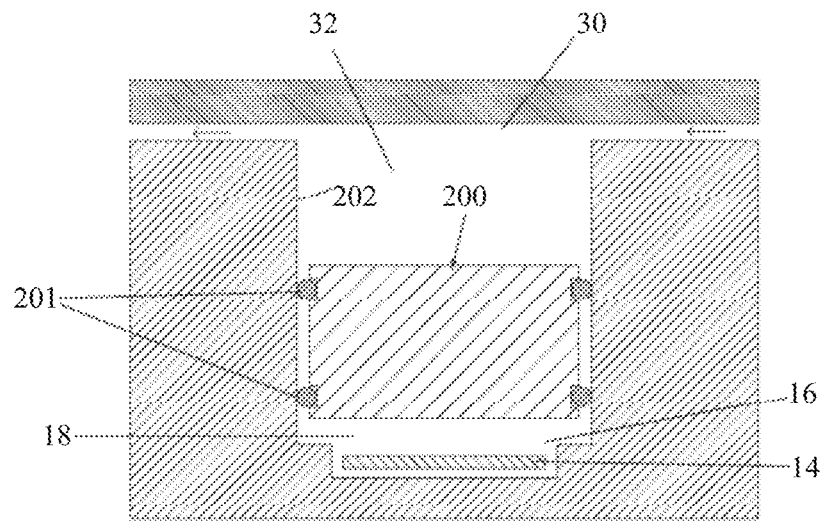
FIG. 11A is a simplified illustration of a piston used as the pushing apparatus for dispensing a substance from dosing chamber (so-called "piston-piston arrangement"), in accordance with a non-limiting embodiment of the present invention.

Reference is now made to FIG. 11A. In this embodiment, instead of a substance-delivery membrane as the pushing apparatus, a piston 200 is the pushing apparatus arranged to push against substance 32 to be delivered from dosing chamber 30. The opposite face of piston 200 is pushed directly by expansion of actuating substance 18 in actuating chamber 16, instead of using a chamber membrane. Actuating substance 18 may be heated by thermal energy source 14, as before. One or more seals 201, such as O-rings, may be used to slidingly seal piston 200 in its travel in a cylinder 202 between actuating chamber 16 and dosing chamber 30.

Figure 11B:
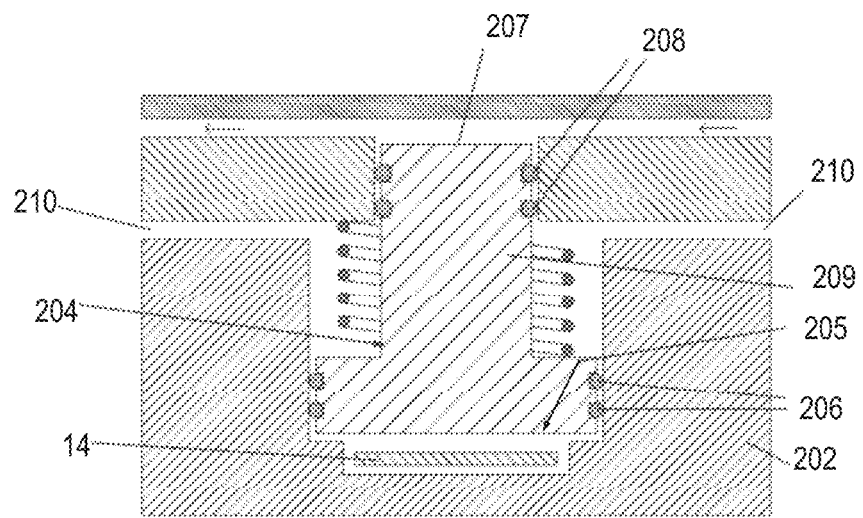
FIG. 11B is a simplified illustration of a variation of the embodiment of FIG. 11A, in which the piston has first and second piston faces of different sizes and has greater separation between the actuating and dosing chambers.

FIG. 11B shows a variation of the embodiment of FIG. 11A. In this embodiment, a piston 204 has a first piston face 205 sealed by one or more seals 206, and a second piston face 207 sealed by one or more seals 208. In the illustrated embodiment, first piston face 205 is larger in diameter than second piston face 207, but the opposite can also be used. In this manner, greater separation is achieved and the shaft 209 of the piston serves as the separator between the two chambers. Ventilation ports 210 may be provided for venting gas or other fluid during the piston travel in its cylinder.

Figure 11C:
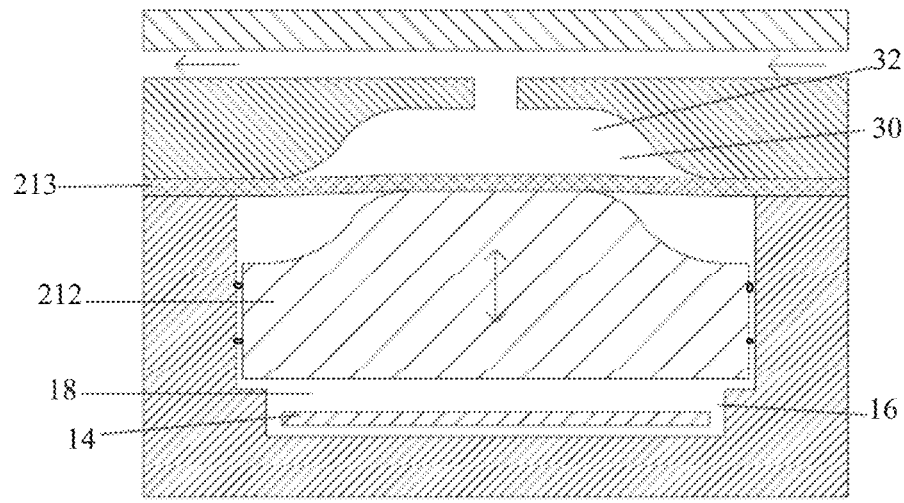
FIG. 11C is a simplified illustration of a piston that pushes against a substance-delivery membrane (so-called "piston-membrane arrangement"), in accordance with a non-limiting embodiment of the present invention.

Reference is now made to FIG. 11C. In this embodiment, a piston 212 is pushed directly by expansion of actuating substance 18 in actuating chamber 16, as in the embodiment of FIG. 11A. The opposite face of piston 212 pushes against substance-delivery membrane 213, which serves as the pushing apparatus to push against and deliver substance 32 from dosing chamber 30.

Figure 11D:
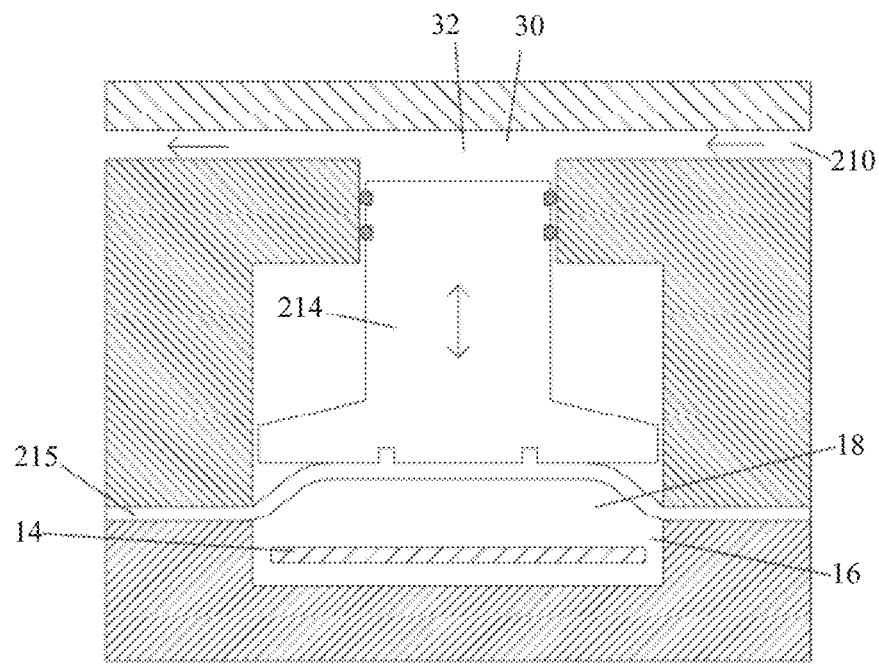
FIG. 11D is a simplified illustration of a piston that is pushed by a chamber membrane (so-called "membrane-piston arrangement"), in accordance with a non-limiting embodiment of the present invention.

Reference is now made to FIG. 11D. In this embodiment, a piston 214 is the pushing apparatus arranged to push against substance 32 to be delivered from dosing chamber 30. The opposite face of piston 200 is pushed by a chamber membrane 215, which is moved by expansion of actuating substance 18 in actuating chamber 16, as described in previous embodiments.

Figure 11E:
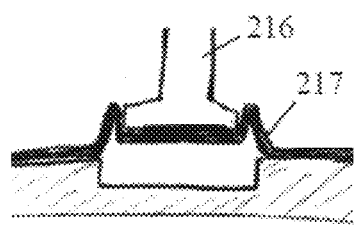
FIG. 11E is a simplified illustration of a piston that abuts against the folds of a membrane in accordance with a non-limiting embodiment of the present invention.

Reference is now made to FIG. 11E. In this embodiment, a piston 216 is mounted in or abuts against the folds (like bellows) of a membrane 217. This arrangement enables a large range of movement with minimal resistance (elastic) force. The membrane 217 may either be the substance-delivery membrane or the chamber membrane or both, and can be used with the separator of previous embodiments instead of piston 216.

In all the embodiments of the invention described herein, the membranes may be elastic or may have sufficient stiffness for applying forces in the direction of either chamber.

Figure 11F:
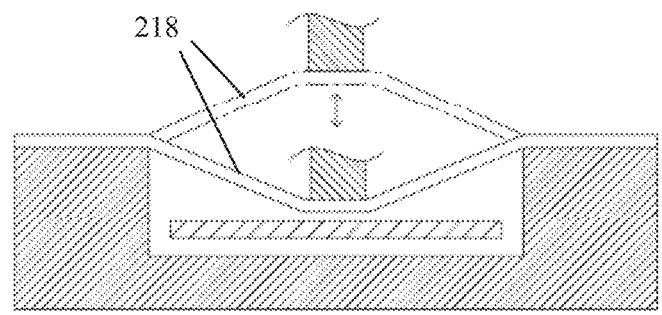
FIG. 11F is a simplified illustration of a Belleville washer used as the pushing apparatus, in accordance with a non-limiting embodiment of the present invention.

Reference is now made to FIG. 11F. In this embodiment, the pushing apparatus is a Belleville washer 218, which can serve as the substance-delivery membrane or the chamber membrane or both. Belleville washer 218 may have different sizes and shapes and may be made of different materials to suit any engineering need.

Figure 12A:
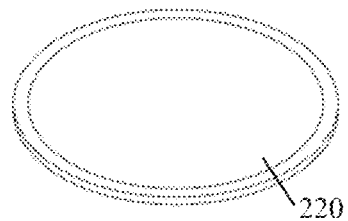
Figure 12B:
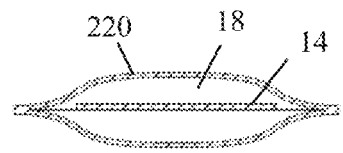
Figure 12C:
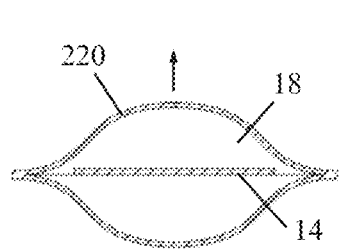
Figure 12D:
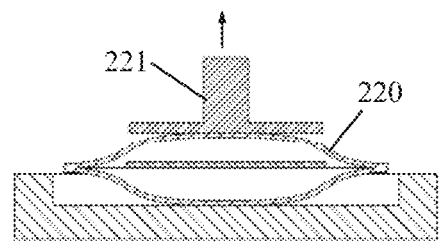

Reference is now made to FIGS. 12A-12D, which illustrate another actuating chamber 220 useful in the present invention. In this embodiment, actuating chamber 220 is constructed as a closed cushion or pliant, resilient closure, made of any suitable resilient or flexible material, such as but not limited to, multilayer foil (such as that described above), polyurethane, polyethylene, cloth from synthetic or natural fibers, and many others. The actuating chamber 220 may be made of two parts sealed around their periphery, such as by adhesive bonding, thermal bonding, welding, and other methods of joining. The actuating substance 18 is disposed in actuating chamber 220 and heated by thermal energy source 14, as before. FIGS. 12B and 12C illustrate actuating chamber 220 respectively before and after actuating substance 18 is heated by thermal energy source 14. FIG. 12D illustrates actuating chamber 220 in its expanded, pressurized state used to push a piston or separator 221.

Figure 13A:
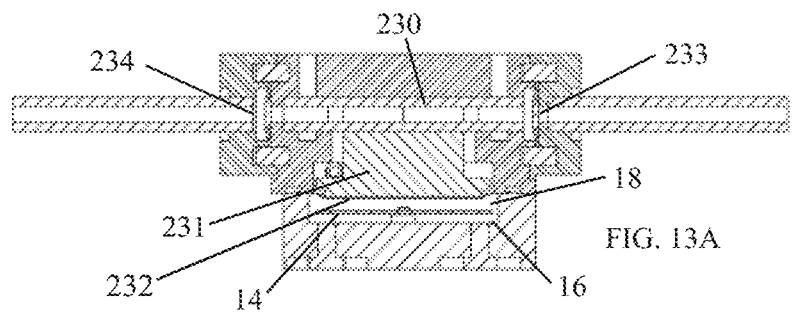
FIGS. 13A-13D are simplified illustrations of a dosing chamber in accordance with another non-limiting embodiment of the present invention, wherein the substance-delivery membrane is in the form of a flexible tube.
Figure 13B:
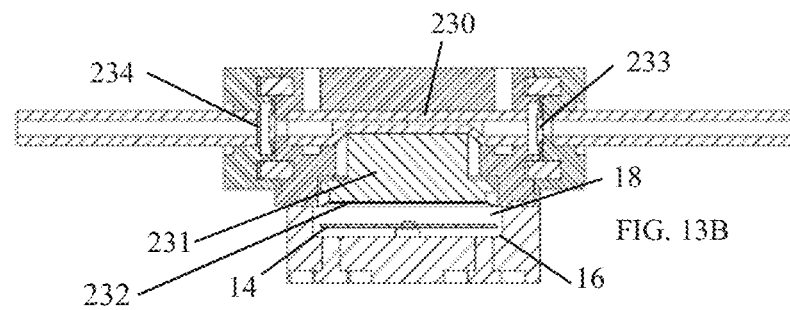
Figure 13C:
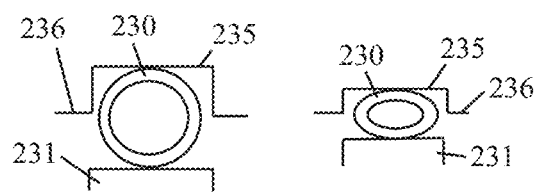
Figure 13D:
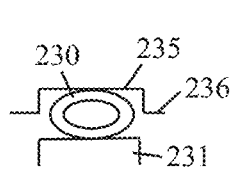

Reference is now made to FIGS. 13A-13D, which illustrate another dosing chamber 230 useful in the present invention. In this embodiment, the substance 32 is expelled from dosing chamber 230 using a separator (piston) 231 and chamber membrane 232 which is actuated by actuating substance 18 heated by thermal energy source 14 in actuating chamber 16, as before. Dosing chamber 230 includes a resilient, flexible tube with a substance inlet 233 and substance outlet 234 (the walls of tube 230 serve as the substance-delivery membrane). The tube 230 is mounted in a housing 235. As seen in FIG. 13C, tube 230 is substantially round (circular) before being pressed by separator 231. As seen in FIG. 13D, tube 230 becomes flattened when pressed by separator 231. For certain substances it may be important to ensure that tube 230 does not get pressed to the point of being completely flattened, e.g., so as not to damage large molecules which may become altered or whose properties may become adversely affected upon excessive pressing forces. To ensure that tube 230 does not get over-pressed, housing 235 may have an abutment (limiter) 236, such as a shoulder, which serves as a stopper against separator 231.

Reference is now made to FIGS. 14A-14F, which illustrate an embodiment for use with devices of the invention that have a needle and cannula, e.g., the embodiments of FIGS. 5C-5H. A needle first punctures the user's skin. The needle runs through a cannula (or the cannula is introduced over the needle). After puncturing, the needle is retracted and the cannula remains as the conduit for drug delivery.

Figure 14A:
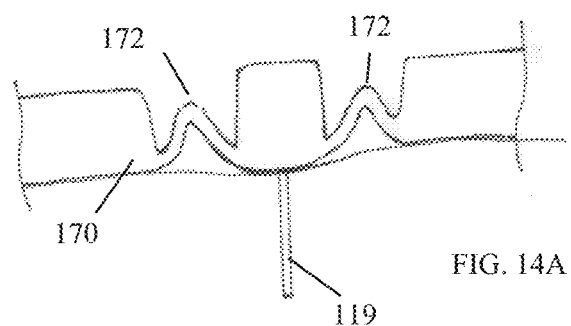
Figure 14B:
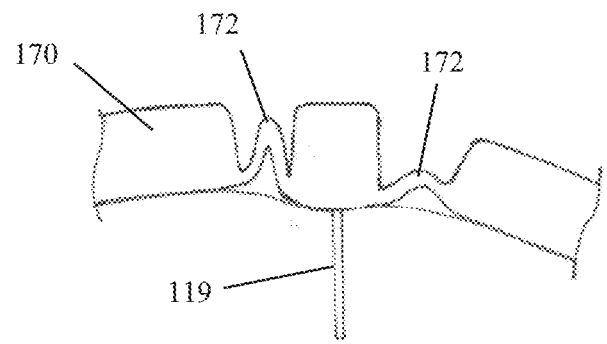
Figure 14C:
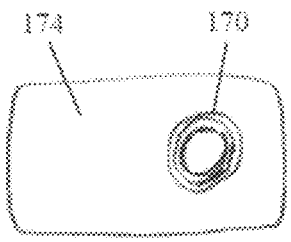
Figure 14D:
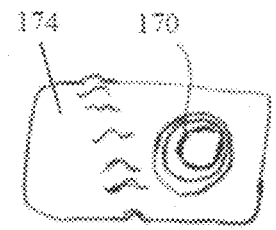
Figure 14E:
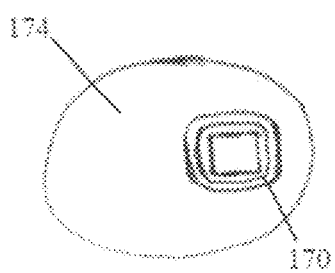
Figure 14F:
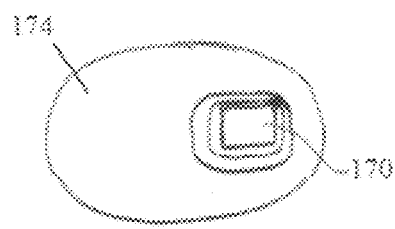

In the embodiment of FIGS. 14A and 14B, the cannula 119 is mounted on a flexible mounting member 170, which may be an elastomeric member with a plurality of folds 172. In FIGS. 14C-14D, flexible mounting member 170 is shown to be generally circular, whereas in FIGS. 14E-14F, flexible mounting member 170 is shown to be generally rectangular with rounded corners. Of course, the invention is not limited to any shape or size. The purpose of flexible mounting member 170 and folds 172 is to compensate for any sideways forces (from bending, stretching and other movements of the skin surface, for example) which may be applied to cannula 119, which would have caused strain to the cannula 119 and discomfort to the user, and may have even forced the cannula out of the skin. The flexible mounting member 170 and folds 172 urge the cannula 119 downwards into the skin.

In FIGS. 14C-14F, flexible mounting member 170 is mounted on a patch 174. Alternatively, flexible mounting member 170 may be part of the flexible patch of FIGS. 5A-5H. In one embodiment, patch 174 is fully flexible and stretchable, which also compensates for skin tension and movement. In an alternative embodiment, patch 174 is rigid or semi-rigid, in which case, flexible mounting member 170 is the sole compensator.

Figure 15A:
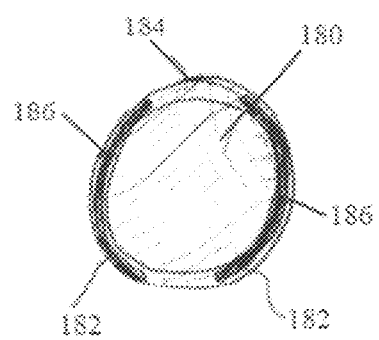
FIGS. 15A-15B are simplified illustrations of a plurality of thermally conducting fibers used to maintain good thermal contact with the actuating substance in the actuating chamber, in accordance with a non-limiting embodiment of the present invention.
Figure 15B:
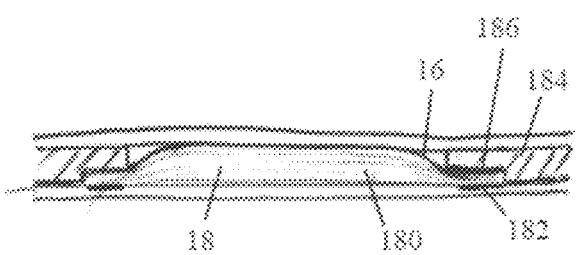

As mentioned above, since the delivery device may be oriented in all kinds of orientations, including upside down, a maintaining element may be included to maintain the actuating substance in conductive thermal contact with the thermal energy source in any gravitational orientation. Reference is now made to FIGS. 15A-15B, which illustrate a further example of such a maintaining element. In this embodiment, the thermal energy source is a plurality of thermally conducting fibers 180 (for example, carbon fibers or carbon cloth), which are disposed in actuating chamber 16. The fibers 180 may be in the form of a pad of any shape (e.g., circular), which is a woven pad or felt pad and the like, with the fibers arranged in any manner, such as weave, felt and the like. As seen in FIG. 15A, the fiber pad periphery may be in electrical contact with electrical contacts 182, for electrical resistance heating of the fibers 180. A clamping ring 184 may fix the fiber pad periphery and ensure good electrical contact with electrical contacts 182. In this manner, the fibers 180 are in excellent thermal contact with actuating substance 18 disposed in actuating chamber 16, so that actuating substance 18 is quickly and efficiently heated by electrical resistance heating of fibers 180. The capillary action of the fibers 180 maintains contact with actuating substance 18 no matter what the orientation of the device. A seal 186 may be provided to fluidly seal actuating substance 18 disposed in actuating chamber 16 and press the fibers onto contacts 182. Accordingly, the thermal energy source is also the maintaining element. The thermal energy source is in intimate contact with the actuating substance with substantially enhance contact area and thermal conductivity.

The invention claimed is:

1. A delivery device comprising:
a dosing chamber for delivering a substance therefrom; and
a housing which includes said dosing chamber;
wherein said housing is mounted on a collar device of an animal, a harness of an animal or a neck strap of an animal, and comprising a flexible and bendable dosing probe that extends from said housing, and wherein said collar device, said harness or said neck strap comprises an inner surface for resting on the animal, an outer surface opposite said inner surface and side edges that extend between said outer and inner surfaces, and said housing is mounted on said outer surface and said probe does not pass through said collar device, said harness or said neck strap, but instead is located adjacent one of said side edges, and wherein an exit outlet of said dosing probe is directed towards fur or skin of the animal on which said collar device overlies.

2. The delivery device according to claim 1, wherein said probe comprises a distal exit slit.

3. The delivery device according to claim 1, wherein said probe is parallel to said one of said side edges.

4. The delivery device according to claim 1, wherein said probe is spaced by a gap from said one of said side edges.

5. A method of substance delivery comprising:
providing a delivery device that comprises a dosing chamber for delivering a substance therefrom, and a housing which includes said dosing chamber;
wherein said housing is mounted on a collar device of an animal, a harness of an animal or a neck strap of an animal, and comprising a flexible and bendable dosing probe that extends from said housing, and wherein said collar device, said harness or said neck strap comprises an inner surface for resting on the animal, an outer surface opposite said inner surface and side edges that extend between said outer and inner surfaces, and said housing is mounted on said outer surface and said probe does not pass through said collar device, said harness or said neck strap, but instead is located adjacent one of said side edges,
placing said delivery device and said collar device on an animal such that an exit outlet of said dosing probe is directed towards fur or skin of the animal on which said collar device overlies; and
using the delivery device to dispense a drug through said exit outlet onto the fur or the skin of the animal to treat a medical condition of the animal.

6. The method according to claim 5, wherein said medical condition comprises a parasite infestation.

7. The method according to claim 5, wherein using the delivery device to dispense the drug comprises pressing said dosing probe against the fur or skin of the animal so as to bend said dosing probe.

* * * * *